(12) United States Patent
Tisdale et al.

(10) Patent No.: US 11,325,978 B2
(45) Date of Patent: May 10, 2022

(54) COMPOSITIONS AND METHODS FOR TREATING BETA-GLOBINOPATHIES

(71) Applicant: The United States of America, as Represented by the Secretary of the Department of Health and Human, Rockville, MD (US)

(72) Inventors: John Fitzgerald Tisdale, Washington, DC (US); Bjorg Gudmundsdottir, Silver Spring, MD (US); Laxminath Tumburu, Bethesda, MD (US)

(73) Assignee: THE UNITED STATES OF AMERICA, AS REPRESENTED BY THE SECRETARY OF THE DEPARTMENT OF HEALTH AND HUMAN SERVICES, Bethesda, MD (US)

(*) Notice: Subject to any disclaimer, the term of this patent is extended or adjusted under 35 U.S.C. 154(b) by 0 days.

(21) Appl. No.: 16/676,369

(22) Filed: Nov. 6, 2019

(65) Prior Publication Data

US 2020/0216545 A1 Jul. 9, 2020

Related U.S. Application Data

(60) Provisional application No. 62/756,497, filed on Nov. 6, 2018.

(51) Int. Cl.
| | | |
|---|---|---|
| *C07K 14/805* | (2006.01) | |
| *C07K 16/28* | (2006.01) | |
| *A61P 7/06* | (2006.01) | |
| *A61K 9/00* | (2006.01) | |
| *A61K 9/08* | (2006.01) | |
| *A61K 9/14* | (2006.01) | |
| *A61K 9/20* | (2006.01) | |
| *A61K 9/48* | (2006.01) | |

(52) U.S. Cl.
CPC ........ *C07K 16/2863* (2013.01); *A61K 9/0019* (2013.01); *A61K 9/0053* (2013.01); *A61K 9/08* (2013.01); *A61K 9/14* (2013.01); *A61K 9/20* (2013.01); *A61K 9/4808* (2013.01); *A61P 7/06* (2018.01)

(58) Field of Classification Search
None
See application file for complete search history.

(56) References Cited

U.S. PATENT DOCUMENTS

| | | | |
|---|---|---|---|
| 4,405,712 A | 9/1983 | Vande Woude et al. | |
| 5,010,175 A | 4/1991 | Rutter et al. | |
| 5,093,246 A | 3/1992 | Cech et al. | |
| 5,288,514 A | 2/1994 | Ellman | |
| 5,506,337 A | 4/1996 | Summerton et al. | |
| 5,519,134 A | 5/1996 | Acevedo et al. | |
| 5,525,735 A | 6/1996 | Gallop et al. | |
| 5,539,083 A | 7/1996 | Cook et al. | |
| 5,549,974 A | 8/1996 | Holmes | |
| 5,569,588 A | 10/1996 | Ashby et al. | |
| 5,593,853 A | 1/1997 | Chen et al. | |
| 6,110,462 A | 8/2000 | Barbas et al. | |
| 2007/0042937 A1* | 2/2007 | Klaus .................. | A61K 31/17 514/13.5 |
| 2007/0299049 A1* | 12/2007 | Coutre .................. | A61P 27/16 514/211.08 |

FOREIGN PATENT DOCUMENTS

| | | | |
|---|---|---|---|
| EP | 0178220 A2 | 4/1986 | |
| WO | 88/04300 A1 | 6/1988 | |
| WO | 88/09810 A1 | 12/1988 | |
| WO | 89/10134 A1 | 11/1989 | |
| WO | 90/11364 A1 | 10/1990 | |
| WO | 91/19735 A1 | 12/1991 | |
| WO | 92/00091 A1 | 1/1992 | |
| WO | 92/06180 A1 | 4/1992 | |
| WO | 92/07943 A1 | 5/1992 | |
| WO | 93/14188 A1 | 7/1993 | |
| WO | 93/19768 A1 | 10/1993 | |
| WO | 93/20221 A1 | 10/1993 | |
| WO | 93/20242 A1 | 10/1993 | |
| WO | 94/06922 A1 | 3/1994 | |
| WO | 94/06923 A1 | 3/1994 | |
| WO | 1997000271 A1 | 1/1997 | |
| WO | 02/086075 A2 | 10/2002 | |
| WO | WO-2012010321 A1 * | 1/2012 | ......... C07K 14/4702 |
| WO | 2016/133910 A1 | 8/2016 | |

OTHER PUBLICATIONS

Stamatoyannopoulos, G. Exp Hematol. Mar. 2005 ; 33(3): 259. doi: 10.1016/j.exphem.2004.11.007.*

Batzer, Mark A. et al., "Enhanced evolutionary PCR using oligonucleotides with inosine at the 3'-terminus", Nucleic Acids Research, 1991, p. 5081, vol. 19, No. 18.

Ohtsuka, Eiko et al., "An alternative approach to deoxyoligonucleotides as hybridization probes by insertion of deoxyinosine at ambiguous codon positions", J. Biol. Chem., 1985, pp. 2605-2608, vol. 260.

Rossolini, Gian Maria et al., "Use of deoxyinosine-containing primers vs degenerate primers for polymerase chain reaction based on ambiguous sequence information", Molecular and Cellular Probes, 1994, pp. 91-98, vol. 8.

Brinster, Ralph L. et al., "Regulation of metallothionein-thymidine kinase fusion plasmids injected into mouse eggs", Nature, Mar. 4, 1982, pp. 39-42, vol. 296.

(Continued)

*Primary Examiner* — Michael Szperka
(74) *Attorney, Agent, or Firm* — McBee Moore & Vanik IP, LLC

(57) ABSTRACT

The present invention provides new compositions and methods useful for the treatment and potential cure of beta-globinopathies such as sickle cell disease and beta-thalassemia by inhibiting the expression and/or activity of RIOK3.

12 Claims, 12 Drawing Sheets

Specification includes a Sequence Listing.

(56) References Cited

OTHER PUBLICATIONS

Paddison, Patrick J. et al., "Short hairpin RNAs (shRNAs) induce sequence-specific silencing in mammalian cells", Genes Dev., 2002, pp. 948-958, vol. 16.
Jones, Peter T. et al., "Replacing the complementarity-determining regions in a human antibody with those from a mouse", Nature, 1986, pp. 522-525, vol. 321.
McCaffrey, Anton P. et al., "RNA interference in adult mice", Nature, 2002, pp. 38-39, vol. 418.
Yu, Jenn-Yah et al., "RNA interference by expression of short-interfering RNAs and hairpin RNAs in mammalian cells", Proc Natl Acad Sci USA, 2002, pp. 6047-6052, vol. 99.
Sarver, Nava et al., "Ribozymes as potential anti-HIV-1 therapeutic agents", Science, Mar. 9, 1990, pp. 1222-1225, vol. 247, No. 4947.
Haseloff, Jim and Wayne L. Gerlach, "Simple RNA enzymes with new and highly specific endoribonuclease activities", Nature, 1988, pp. 585-591, vol. 334.
Zaug, Arthur J. et al., "A labile phosphodiester bond at the ligation junction in a circular intervening sequence RNA", Science, 1984, pp. 574-578, vol. 224.
Gudmundsdottir et al. "POGZ is Required for Silencing Mouse Embryonic β-like Hemoglobin and Human Fetal Hemoglobin Expression", Cell Reports, 2018, pp. 3236-3248, vol. 23.
Zaug, Arthur J. and Thomas R. Cech, "The intervening sequence RNA of Tetrahymena is an enzyme", Science, 1986, pp. 470-475, vol. 231.
Zaug, Arthur J. et al., "The Tetrahymena ribozyme acts like an RNA restriction endonuclease", Nature, Dec. 4, 1986, pp. 429-433, vol. 324.
Been, Michael D. and Cech, Thomas R., "One binding site determines sequence specificity of Tetrahymena pre-rRNA self-splicing, trans-splicing, and RNA enzyme activity", Cell, Oct. 24, 1986, pp. 207-216, vol. 47.
Beaucage, S.L. et al., "Deoxynucleoside phosphoramidites—A new class of key intermediates for deoxypolynucleotide synthesis", Tetrahedron Letters, 1981, pp. 1859-1862, vol. 22, No. 20.
Needham-Vandevanter, Donald R. et. al., "Characterization of an adduct between CC-1065 and a defined oligodeoxynucleotide duplex", Nucleic Acids Research, 1984, pp. 6159-6168, vol. 12, No. 15.
Pearson, J.D. and Regnier, F.E., High-performance anion-exchange chromatography of oligonucleotides, Journal of Chromatography, 1983, pp. 137-149, vol. 255.
Wallace, R. Bruce et al., "A set of synthetic oligodeoxyribonucleotide primers for DNA sequencing in the plasmid vector pBR322", Gene, 1981, pp. 21-26, vol. 16, No. 1-3.
Ledford, Heidi, "Riding the CRISPR Wave", Nature, 2016, pp. 156-159, vol. 531, No. 7593.
Furka, Arpad et al., "General method for rapid synthesis of multicomponent peptide mixtures", Int. J. Pept. Protein Res., 1991, pp. 487-493, vol. 37, No. 6.
Houghten, Richard A. et al., "Generation and use of synthetic peptide combinatorial libraries for basic research and drug discovery", Nature, Nov. 7, 1991, p. 84-88, vol. 354, No. 6348.
Liang, Rui et al., "Parallel synthesis and screening of a solid phase carbohydrate library", Science, 1996, pp. 1520-1522, vol. 274.
Kohler and Milstein, "Continuous cultures of fused cells secreting antibody of predefined specificity", Nature, Aug. 7, 1975, pp. 495-497, vol. 256.
Huse, William D. et a., "Generation of a large combinatorial library of the immunoglobulin repertoire in phage lambda", Science, Dec. 8, 1989, pp. 1275-1281, vol. 246.
Ward, E. Sally et al., "Binding activities of a repertoire of single immunoglobulin variable domains secreted from *Escherichia coli*", Nature, Oct. 12, 1989, pp. 544-546, vol. 341.
Kohler and Milstein, "Derivation of specific antibody-producing tissue culture and tumor lines by cell fusion", European Journal of Immunology, 1976, pp. 511-519, vol. 6, No. 7.
Letsinger, Robert et al., "Cholesteryl-conjugated oligonucleotides: Synthesis, properties, and activity as inhibitors of replication of human immunodeficiency virus in cell culture", Proc Natl Acad Sci USA, Sep. 1989, pp. 5553-6556, vol. 86, No. 17.
Lemaitre, Mac et al., Specific antiviral activity of a poly(L-lysine)-conjugated oligodeoxyribonucleotide sequence complementary to vesicular stomatitis virus N protein mRNA initiation site, Proc Natl Acad Sci USA, 1987, pp. 648-652, vol. 84, No. 3.
Van Der Krol, Alexander R. et al., "Inhibition of flower pigmentation by antisense CHS genes: promoter and minimal sequence requirements for the antisense effect", Plant Molecular Biology, 1990, pp. 457-466, vol. 14.
Zon, Gerald, "Oligonucleotide analogues as potential chemotherapeutic agents", Pharmaceutical Research, 1988, pp. 539-549, vol. 5, No. 9.
Stein, C.A. et al., "Physicochemical properties of phosphorothioate oligodeoxynucleotides", Nucleic Acids Res., 1988, pp. 3209-3221, vol. 16, No. 8.
Sarin, Prem S. et al., Inhibition of acquired immunodeficiency syndrome virus by oligodeoxynucleoside methylphosphonates, Proc Natl Acad Sci USA, Oct. 1988, pp. 7448-7451, vol. 85, No. 20.
Benoist and Chambon, "In vivo sequence requirements of the SV40 early promoter region", Nature, Mar. 26, 1981, pp. 304-310, vol. 290.
Yamamoto, Tadashi et al., "Identification of a functional promoter in the long terminal repeat of Rous sarcoma virus", Cell, Dec. 1980, pp. 787-797, vol. 22.
Wagner, Michael J. et al., "Nucleotide sequence of the thymidine kinase gene of herpes simplex virus type 1", Proc Natl Acad Sci USA, Mar. 1981, pp. 1441-1445, vol. 78, No. 3.
DeWitt, Sheila Hobbs et al., "'Diversomers': An approach to nonpeptide, nonoligomeric chemical diversity", Proc Natl Acad Sci USA, Aug. 1993, pp. 6909 6913, vol. 90, No. 15.
Hagihara, Masahiko et al., "Vinylogous polypeptides: an alternative peptide backbone", J. Amer. Chem. Soc., 1992, pp. 6568-6570, vol. 114.
Hirschmann, Ralph et al., "Nonpeptidal peptidomimetics with .beta.-D-glucose scaffolding. A partial somatostatin agonist bearing a close structural relationship to a potent, selective substance P antagonist", J. Amer. Chem. Soc., 1992, pp. 9217-9218, vol. 114.
Chen, Chixu et al., "'Analogous' organic synthesis of small-compound libraries: validation of combinatorial chemistry in small-molecule synthesis", Journal of the American Chemical Society, 1994, pp. 2661-2662, vol. 116, No. 6.
Cho, Charles Y. et al., "An unnatural biopolymer", Science, 1993, pp. 1303-1305, vol. 261, No. 5126.
Campbell and Bermak, "Phosphonate ester synthesis using a modified Mitsunobu condensation", Journal of Organic Chemistry, 1994, pp. 658-660, vol. 59, No. 3.
Vaughan, Tristan et al., "Human antibodies with sub-nanomolar affinities isolated from a large non-immunized phage display library", Nature Biotechnology, Mar. 1996, pp. 309-314, vol. 14, No. 3.
Baum, Rudy, "Solid-phase synthesis of benzodiazepines", C&EN, 1993, pp. 33-34, vol. 71, No. 3.
Langer, Robert, "New methods of drug delivery", Science, Sep. 28, 1990, pp. 1527-1533, vol. 249, No. 4976.
Miller, A. Dusty, "Human gene therapy comes of age", Nature, Jun. 11, 1992, pp. 455-460, vol. 357, No. 6378.
Mulligan, Richard C. "The basic science of gene therapy", Science, May 14, 1993, pp. 926-932, vol. 260, No. 5110.
Wu, George Y. et al., "Receptor-mediated gene delivery and expression in vivo", The Journal of Biological Chemistry, Oct. 15, 1988, p. 14621-14624, vol. 263, No. 29.
Lan, Hui Y. et al., "Inhibition of Renal Fibrosis by Gene Transfer of Inducible Smad7 Using Ultrasound-Microbubble System in Rat UUO Model", J. Am Soc Nephrol, 2003, pp. 1535-1548, vol. 14, No. 6.
Curiel, David T. et al., "Adenovirus enhancement of transferrin-polylysine-mediated gene delivery", Proc Natl Acad Sci U.S.A., 1991, pp. 8850-8854, vol. 88, No. 19.
Plank, Christian et al., "The influence of endosome-disruptive peptides on gene transfer using synthetic virus-like gene transfer systems", The Journal of Biological Chemistry, 1994, p. 12918-12924, vol. 269, No. 17.

(56) References Cited

OTHER PUBLICATIONS

Government-Owned Inventions; Availability for Licensing, 83 Fed. Reg. 58265 (Nov. 19, 2018).
Mann, Richard et al., "Construction of a retrovirus packaging mutant and its use to produce helper-free defective retrovirus", Cell, May 1983, pp. 153-159, vol. 33, No. 1.
Mishra, Dhruva Kumar et al., "Global methylation pattern of genes in androgen-sensitive and androgen-independent prostate cancer cells", Molecular Cancer Therapeutics, 2010, pp. 33-45, vol. 9, No. 1.
Cone, Roger D. and Richard C. Mulligan, "High-efficiency gene transfer into mammalian cells: Generation of helper-free recombinant retrovirus with broad mammalian host range", Proc Natl Acad Sci U.S.A., Oct. 1984, pp. 3349-6353, vol. 81, 20.
Shan, Jingxuan et al. RIOK3 interacts with caspase-10 and negatively regulates the NF-kappaB signaling pathway, Mol Cell Biochem, Dec. 2009, pp. 113-120, vol. 332, No. 1-2.
Miller, A. Dusty et al., "Improved Retroviral Vectors for Gene Transfer and Expression", BioTechniques, Oct. 1989, pp. 980-990, vol. 7.
Kimmelman, Alec C. et al., "Genomic alterations link Rho family of GTPases to the highly invasive phenotype of pancreas cancer", Proc Natl Acad Sci USA, Dec. 9, 2008, p. 19372-19377, vol. 105, No. 49.
Miller, A. Dusty et al., "Construction and properties of retrovirus packaging cells based on gibbon ape leukemia virus", Journal of Virology, May 1991, pp. 2220-2224, vol. 65, No. 5.
Danos, Olivier and Richard C. Mulligan, "Safe and efficient generation of recombinant retroviruses with amphotropic and ecotropic host ranges", Proc Natl Acad Sci USA, Sep. 1988, pp. 6460-6464, vol. 85, No. 17.
Good, Norman E. et al., "Hydrogen Ion Buffers for Biological Research", Biochemistry, Feb. 2, 1966, pp. 467-477, vol. 5, No. 2.
Nolta, Jan A. et al., "Transduction of pluripotent human hematopoietic stem cells demonstrated by clonal analysis after engraftment in immune-deficient mice", Proc Natl Acad. Sci USA, 1996, pp. 2414-2419, vol. 93, No. 6.
Koc, Omer N. et al., "Transfer of Drug Resistance Genes Into Hematopoietic Progenitors to Improve Chemotherapy Tolerance", Seminars in Oncology, 1996, pp. 46-65, vol. 23, No. 1.
Raper, Steven E. et al. "Safety and feasibility of liver-directed ex vivo gene therapy for homozygous familial hypercholesterolemia", Annals of Surgery, 1996, pp. 116-126, vol. 223, No. 2.
Dalesandro, Joy et al., "Gene Therapy for Donor Hearts: Ex Vivo Liposome-Mediated Transfection", The Journal of Thoracic and Cardiovascular Surgery, 1996, pp. 416-422, vol. 111, No. 2.
Makarov, Sergei et al., "Suppression of experimental arthritis by gene transfer of interleukin 1 receptor antagonist cDNA", Proc Natl Acad Sci USA, Jan. 1996, pp. 402-406, vol. 93, No. 1.

Menzel, Stephan et al., "A QTL influencing F cell production maps to a gene encoding a zinc-finger protein on chromosome 2p15", Nature Genetics, 2007, pp. 1197-1199, vol. 39, No. 10.
Masuda, Takeshi et al., Transcription factors LRF and BCL11A independently repress expression of fetal hemoglobin, Science, 2016, pp. 285-289, vol. 351, No. 6270.
Davis, Mindy I. et al., "Comprehensive analysis of kinase inhibitor selectivity", Nature Biotechnology, 2011, pp. 1046-1051, vol. 29, No. 11.
Website: guidetopharmacology.org/GRAC/ObjectScreenDisplayForward?objectId=2188&familyId=538&screenId=2; Downloaded on Oct. 26, 2020.
Weinberg, Florian et al., "The Atypical Kinase RIOK1 Promotes Tumor Growth and Invasive Behavior", EBioMedicine, 2017, pp. 79-97, vol. 20.
Maasalu, Katre et al., "Transcriptional landscape analysis identifies differently expressed genes involved in follicle-stimulating hormone induced postmenopausal osteoporosis", Exp Biol Med (Maywood), 2017, pp. 203-213, vol. 242, No. 2.
Oshiumi, Hiroyuki et al., "Accessory Factors of Cytoplasmic Viral RNA Sensors Required for Antiviral Innate Immune Response", Frontiers in Immunology, May 25, 2016, vol. 7, No. 200.
Haring, Robin et al., "Associations between Serum Sex Hormone Concentrations and Whole Blood Gene Expression Profiles in the General Population", PLoS One, 2015, e0127466, vol. 10, No. 5.
Takashima, Ken et al., "RIOK3-mediated phosphorylation of MDA5 interferes with its assembly and attenuates the innate immune response", Cell Reports, 2015, pp. 192-200, vol. 11, No. 2.
Singleton, DC et al., "Hypoxic regulation of RIOK3 is a major mechanism for cancer cell invasion and metastasis", Oncogene, 2015, 4713-4722, vol. 34, No. 36.
Feng, Jun et al., "RIOK3 is an Adaptor Protein Required for IRF3-Mediated Antiviral Type I Interferon Production", Journal of Virology, Jul. 2014, pp. 7987-7997, vol. 88, No. 14.
Tariki, Melanie et al., "RIO kinase 3 acts as a SUFU-dependent positive regulator of Hedgehog signaling", Cellular Signalling, 2013, pp. 2668-2675, vol. 25, No. 12.
Baumas, Kamila et al., "Human RioK3 is a novel component of cytoplasmic pre-40S pre-ribosomal particles", RNA Biology, 2012, pp. 162-174, vol. 9, No. 2.
Zhang, Lingbo et al., "miR-191 regulates mouse erythroblast enucleation by down-regulating Riok3 and Mxi1", Genes Dev., 2011, pp. 119-124, vol. 25, No. 2.
Kalinina, Tatyana et al., "Establishment and characterization of a new human pancreatic adenocarcinoma cell line with high metastatic potential to the lung", BMC Cancer, 2010, 10: 295.
Taher, Ali et al., "Efficacy and safety of ruxolitinib in regularly transfused patients with thalassemia: results from a phase 2a study", Campus of Haematology, Blood, 2018, pp. 263-265, vol. 131, No. 2.
Mohamed, Ahmed A. et al. "Identification of a small molecule that selectively inhibits ERG-positive cancer cell growth", Cancer Research, 2018, pp. 3659-3671, vol. 78, No. 13.

* cited by examiner

Donor 14
ShRNA KD Empty vector.

Donor 14
shRNA RIOK3 KD.

Figure 10

| Target used in screen: RIOK3 | | | | | | | | |
|---|---|---|---|---|---|---|---|---|
| Ligand | Sp. | Type | Action | Affinity (-log₁₀) | Units | Affinity (nM) | Units |
| lestaurtinib | | Hs | Inhibitor | Inhibition | 8.1 | $pK_d$ | 7.7 | $K_d$ |
| KW-2449 | | Hs | Inhibitor | Inhibition | 7.2 | $pK_d$ | 61.0 | $K_d$ |
| staurosporine | | Hs | Inhibitor | Inhibition | 7.1 | $pK_d$ | 76.0 | $K_d$ |
| fedratinib | | Hs | Inhibitor | Inhibition | 7.0 | $pK_d$ | 91.0 | $K_d$ |
| tamatinib | | Hs | Inhibitor | Inhibition | 6.7 | $pK_d$ | 210.0 | $K_d$ |
| PHA-665752 | | Hs | Inhibitor | Inhibition | 6.4 | $pK_d$ | 390.0 | $K_d$ |
| midostaurin | | Hs | Inhibitor | Inhibition | 6.4 | $pK_d$ | 420.0 | $K_d$ |
| toxaesertib | | Hs | Inhibitor | Inhibition | 6.2 | $pK_d$ | 600.0 | $K_d$ |
| ruboxistaurin | | Hs | Inhibitor | Inhibition | 6.2 | $pK_d$ | 650.0 | $K_d$ |
| A-674563 | | Hs | Inhibitor | Inhibition | 6.2 | $pK_d$ | 690.0 | $K_d$ |
| dovitinib | | Hs | Inhibitor | Inhibition | 6.2 | $pK_d$ | 690.0 | $K_d$ |
| axitinib | | Hs | Inhibitor | Inhibition | 6.0 | $pK_d$ | 1000.0 | $K_d$ |
| bosutinib | | Hs | Inhibitor | Inhibition | 5.8 | $pK_d$ | 1600.0 | $K_d$ |
| JNJ-28312141 | | Hs | Inhibitor | Inhibition | 5.7 | $pK_d$ | 2000.0 | $K_d$ |
| ruxolitinib | | Hs | Inhibitor | Inhibition | 5.7 | $pK_d$ | 2000.0 | $K_d$ |
| GSK-461364A | | Hs | Inhibitor | Inhibition | 5.6 | $pK_d$ | 2300.0 | $K_d$ |
| BMS-345541 | | Hs | Inhibitor | Inhibition | <5.5 | $pK_d$ | >3000.0 | $K_d$ |

SEQUENCE LISTING

<160> NUMBER OF SEQ ID NOS: 4

<210> SEQ ID NO 1
<211> LENGTH: 1560
<212> TYPE: DNA
<213> ORGANISM: Homo sapiens

<400> SEQUENCE: 1

```
atggatctgg taggagtggc atcgcctgag cccgggacgg cagcggcctg ggacccagc      60
aagtgtccat gggctattcc tcaaaataca atatcttgtt ctttggctga tgtaatgagt    120
gaacagctgg ccaaagaatt gcagttagaa gaagaagctg ccgttttttcc tgaagttgct   180
gttgctgaag gaccatttat tactggagaa acattgata cttccagtga ccttatgctg     240
gctcagatgc tacagatgga atatgacaga gaatatgatg cacagcttag gcgtgaagaa    300
aaaaaattca atggagatag caaagtttcc atttcctttg aaaattatcg aaaagtgcat    360
ccttatgaag acagcgatag ctctgaagat gaggttgact ggcaggatac tcgtgatgat    420
ccctacagac cagcaaaacc ggttcccact cctaaaaagg ctttattgg aaaaggaaaa     480
gatatcacca ccaaacatga tgaagtagta tgtgggagaa agaacacagc aagaatggaa    540
aattttgcac ctgagtttca ggtaggagat ggaattggaa tggatttaaa actatcaaac    600
catgttttca atgctttaaa acaacatgcc tactcagaag aacgtcgaag tgcccgccta    660
catgagaaaa aggagcattc tacagcagaa aaagcagttg atcctaagac acgtttactt    720
atgtataaaa tggtcaactc tggaatgttg agacaatca ctggctgtat tagtacagga     780
aaggagtctg ttgtctttca tgcatatgga gggagcatgg aggatgaaaa ggaagatagt    840
aaagttatac ctacagaatg tgccatcaag gtatttaaaa caacccttaa tgaatttaag    900
aatcgtgaca atatattaa agatgatttc aggtttaaag atcgcttcag taaactaaat    960
ccacgtaaga tcatccgcat gtgggcagaa aaagaaatgc acaatctcgc aagaatgcag   1020
agagctggaa ttccttgtcc aacagttgta ctactgaaga aacacatttt agttatgtct   1080
tttattggcc atgatcaagt tccagccccct aaattaaaag aagtaaagct caatagtgaa   1140
gaaatgaaag aagcctacta tcaaactctt catttgatgc ggcagttata tcatgaatgt   1200
acgcttgtcc atgctgacct cagtgagtat aacatgctgt ggcatgctgg aaaggtctgg   1260
ttgatcgatg tcagtcagtc agtagaacct acccaccctc acggcctgga gttcttgttc   1320
cgggactgca ggaatgtctc gcagtttttc cagaaaggag gagtcaagga agcccttagt   1380
gaacgagaac tcttcaatgc tgtttcaggc ttaaacatca cagcagataa tgaagctgat   1440
tttttagctg agatagaagc tttggagaaa atgaatgaag atcacgttca gaagaatgga   1500
aggaaagctg cttcattttt gaaagatgat ggagacccac cactactata tgatgaatag   1560
```

<210> SEQ ID NO 2
<211> LENGTH: 519
<212> TYPE: PRT
<213> ORGANISM: Homo sapiens

<400> SEQUENCE: 2

```
Met Asp Leu Val Gly Val Ala Ser Pro Glu Pro Gly Thr Ala Ala Ala
 1               5                  10                  15

Trp Gly Pro Ser Lys Cys Pro Trp Ala Ile Pro Gln Asn Thr Ile Ser
                20                  25                  30

Cys Ser Leu Ala Asp Val Met Ser Glu Gln Leu Ala Lys Glu Leu Gln
            35                  40                  45
```

```
Leu Glu Glu Ala Ala Val Phe Pro Glu Val Ala Val Glu Gly
 50                  55                  60

Pro Phe Ile Thr Gly Glu Asn Ile Asp Thr Ser Ser Asp Leu Met Leu
 65                  70                  75                  80

Ala Gln Met Leu Gln Met Glu Tyr Asp Arg Glu Tyr Asp Ala Gln Leu
                 85                  90                  95

Arg Arg Glu Glu Lys Lys Phe Asn Gly Asp Ser Lys Val Ser Ile Ser
            100                 105                 110

Phe Glu Asn Tyr Arg Lys Val His Pro Tyr Glu Asp Ser Asp Ser Ser
        115                 120                 125

Glu Asp Glu Val Asp Trp Gln Asp Thr Arg Asp Asp Pro Tyr Arg Pro
130                 135                 140

Ala Lys Pro Val Pro Thr Pro Lys Lys Gly Phe Ile Gly Lys Gly Lys
145                 150                 155                 160

Asp Ile Thr Thr Lys His Asp Glu Val Val Cys Gly Arg Lys Asn Thr
                165                 170                 175

Ala Arg Met Glu Asn Phe Ala Pro Glu Phe Gln Val Gly Asp Gly Ile
            180                 185                 190

Gly Met Asp Leu Lys Leu Ser Asn His Val Phe Asn Ala Leu Lys Gln
        195                 200                 205

His Ala Tyr Ser Glu Glu Arg Arg Ser Ala Arg Leu His Glu Lys Lys
        210                 215                 220

Glu His Ser Thr Ala Glu Lys Ala Val Asp Pro Lys Thr Arg Leu Leu
225                 230                 235                 240

Met Tyr Lys Met Val Asn Ser Gly Met Leu Glu Thr Ile Thr Gly Cys
                245                 250                 255

Ile Ser Thr Gly Lys Glu Ser Val Val Phe His Ala Tyr Gly Gly Ser
            260                 265                 270

Met Glu Asp Glu Lys Glu Asp Ser Lys Val Ile Pro Thr Glu Cys Ala
        275                 280                 285

Ile Lys Val Phe Lys Thr Thr Leu Asn Glu Phe Lys Asn Arg Asp Lys
290                 295                 300

Tyr Ile Lys Asp Asp Phe Arg Phe Lys Asp Arg Phe Ser Lys Leu Asn
305                 310                 315                 320

Pro Arg Lys Ile Ile Arg Met Trp Ala Glu Lys Glu Met His Asn Leu
                325                 330                 335

Ala Arg Met Gln Arg Ala Gly Ile Pro Cys Pro Thr Val Val Leu Leu
            340                 345                 350

Lys Lys His Ile Leu Val Met Ser Phe Ile Gly His Asp Gln Val Pro
        355                 360                 365

Ala Pro Lys Leu Lys Glu Val Lys Leu Asn Ser Glu Glu Met Lys Glu
370                 375                 380

Ala Tyr Tyr Gln Thr Leu His Leu Met Arg Gln Leu Tyr His Glu Cys
385                 390                 395                 400

Thr Leu Val His Ala Asp Leu Ser Glu Tyr Asn Met Leu Trp His Ala
                405                 410                 415

Gly Lys Val Trp Leu Ile Asp Val Ser Gln Ser Val Glu Pro Thr His
            420                 425                 430

Pro His Gly Leu Glu Phe Leu Phe Arg Asp Cys Arg Asn Val Ser Gln
        435                 440                 445

Phe Phe Gln Lys Gly Gly Val Lys Glu Ala Leu Ser Glu Arg Glu Leu
450                 455                 460

Phe Asn Ala Val Ser Gly Leu Asn Ile Thr Ala Asp Asn Glu Ala Asp
```

```
                 465                 470                 475                 480
Phe Leu Ala Glu Ile Glu Ala Leu Glu Lys Met Asn Glu Asp His Val
                    485                 490                 495

Gln Lys Asn Gly Arg Lys Ala Ala Ser Phe Leu Lys Asp Asp Gly Asp
                500                 505                 510

Pro Pro Leu Leu Tyr Asp Glu
            515

<210> SEQ ID NO 3
<211> LENGTH: 503
<212> TYPE: PRT
<213> ORGANISM: Homo sapiens

<400> SEQUENCE: 3

Met Asp Leu Val Gly Val Ala Ser Pro Glu Pro Gly Thr Ala Ala
1               5                   10                  15

Trp Gly Pro Ser Lys Cys Pro Trp Ala Ile Pro Gln Asn Thr Ile Ser
                20                  25                  30

Cys Ser Leu Ala Asp Val Met Ser Glu Gln Leu Ala Lys Glu Leu Gln
                35                  40                  45

Leu Glu Glu Ala Ala Val Phe Pro Glu Val Ala Asp Leu Met Leu
    50                  55                  60

Ala Gln Met Leu Gln Met Glu Tyr Asp Arg Glu Tyr Asp Ala Gln Leu
65                  70                  75                  80

Arg Arg Glu Glu Lys Lys Phe Asn Gly Asp Ser Lys Val Ser Ile Ser
                85                  90                  95

Phe Glu Asn Tyr Arg Lys Val His Pro Tyr Glu Asp Ser Asp Ser Ser
                100                 105                 110

Glu Asp Glu Val Asp Trp Gln Asp Thr Arg Asp Asp Pro Tyr Arg Pro
            115                 120                 125

Ala Lys Pro Val Pro Thr Pro Lys Lys Gly Phe Ile Gly Lys Gly Lys
        130                 135                 140

Asp Ile Thr Thr Lys His Asp Glu Val Val Cys Gly Arg Lys Asn Thr
145                 150                 155                 160

Ala Arg Met Glu Asn Phe Ala Pro Glu Phe Gln Val Gly Asp Gly Ile
                165                 170                 175

Gly Met Asp Leu Lys Leu Ser Asn His Val Phe Asn Ala Leu Lys Gln
            180                 185                 190

His Ala Tyr Ser Glu Glu Arg Ser Ala Arg Leu His Glu Lys Lys
        195                 200                 205

Glu His Ser Thr Ala Glu Lys Ala Val Asp Pro Lys Thr Arg Leu Leu
    210                 215                 220

Met Tyr Lys Met Val Asn Ser Gly Met Leu Glu Thr Ile Thr Gly Cys
225                 230                 235                 240

Ile Ser Thr Gly Lys Glu Ser Val Val Phe His Ala Tyr Gly Gly Ser
                245                 250                 255

Met Glu Asp Glu Lys Glu Asp Ser Lys Val Ile Pro Thr Glu Cys Ala
            260                 265                 270

Ile Lys Val Phe Lys Thr Thr Leu Asn Glu Phe Lys Asn Arg Asp Lys
        275                 280                 285

Tyr Ile Lys Asp Asp Phe Arg Phe Lys Asp Arg Phe Ser Lys Leu Asn
    290                 295                 300

Pro Arg Lys Ile Ile Arg Met Trp Ala Glu Lys Glu Met His Asn Leu
305                 310                 315                 320
```

```
Ala Arg Met Gln Arg Ala Gly Ile Pro Cys Pro Thr Val Val Leu Leu
            325                 330                 335

Lys Lys His Ile Leu Val Met Ser Phe Ile Gly His Asp Gln Val Pro
        340                 345                 350

Ala Pro Lys Leu Lys Glu Val Lys Leu Asn Ser Glu Glu Met Lys Glu
            355                 360                 365

Ala Tyr Tyr Gln Thr Leu His Leu Met Arg Gln Leu Tyr His Glu Cys
    370                 375                 380

Thr Leu Val His Ala Asp Leu Ser Glu Tyr Asn Met Leu Trp His Ala
385                 390                 395                 400

Gly Lys Val Trp Leu Ile Asp Val Ser Gln Ser Val Glu Pro Thr His
                405                 410                 415

Pro His Gly Leu Glu Phe Leu Phe Arg Asp Cys Arg Asn Val Ser Gln
            420                 425                 430

Phe Phe Gln Lys Gly Val Lys Glu Ala Leu Ser Glu Arg Glu Leu
        435                 440                 445

Phe Asn Ala Val Ser Gly Leu Asn Ile Thr Ala Asp Asn Glu Ala Asp
    450                 455                 460

Phe Leu Ala Glu Ile Glu Ala Leu Glu Lys Met Asn Glu Asp His Val
465                 470                 475                 480

Gln Lys Asn Gly Arg Lys Ala Ala Ser Phe Leu Lys Asp Asp Gly Asp
                485                 490                 495

Pro Pro Leu Leu Tyr Asp Glu
            500

<210> SEQ ID NO 4
<211> LENGTH: 516
<212> TYPE: PRT
<213> ORGANISM: Homo sapiens

<400> SEQUENCE: 4

Met Asp Leu Val Gly Val Ala Ser Pro Glu Pro Gly Thr Ala Ala Ala
1               5                   10                  15

Trp Gly Pro Ser Lys Cys Pro Trp Ala Ile Pro Gln Asn Thr Ile Ser
            20                  25                  30

Cys Ser Leu Ala Asp Val Met Ser Glu Gln Leu Ala Lys Glu Leu Gln
        35                  40                  45

Leu Glu Glu Glu Ala Ala Val Phe Pro Glu Val Ala Val Ala Glu Gly
    50                  55                  60

Pro Phe Ile Thr Gly Glu Asn Ile Asp Thr Ser Ser Asp Leu Met Leu
65                  70                  75                  80

Ala Gln Met Leu Gln Met Glu Tyr Asp Arg Glu Tyr Asp Ala Gln Leu
                85                  90                  95

Arg Arg Glu Glu Lys Lys Phe Asn Gly Asp Ser Lys Val Ser Ile Ser
            100                 105                 110

Phe Glu Asn Tyr Arg Lys Val His Pro Tyr Glu Asp Ser Asp Ser Ser
        115                 120                 125

Glu Asp Glu Val Asp Trp Gln Asp Thr Arg Asp Pro Tyr Arg Pro
    130                 135                 140

Ala Lys Pro Val Pro Thr Pro Lys Lys Gly Phe Ile Gly Lys Gly Lys
145                 150                 155                 160

Asp Ile Thr Thr Lys His Asp Glu Val Val Cys Gly Arg Lys Asn Thr
                165                 170                 175

Ala Arg Met Glu Asn Phe Ala Pro Glu Phe Gln Val Gly Asp Gly Ile
            180                 185                 190
```

-continued

```
Gly Met Asp Leu Lys Leu Ser Asn His Val Phe Asn Ala Leu Lys Gln
        195                 200                 205

His Ala Tyr Ser Glu Glu Arg Arg Ser Ala Arg Leu His Glu Lys Lys
    210                 215                 220

Glu His Ser Thr Ala Glu Lys Ala Val Asp Pro Lys Thr Arg Leu Leu
225                 230                 235                 240

Met Tyr Lys Met Val Asn Ser Gly Met Leu Glu Thr Ile Thr Gly Cys
            245                 250                 255

Ile Ser Thr Gly Lys Glu Ser Val Val Phe His Ala Tyr Gly Gly Ser
            260                 265                 270

Met Glu Asp Glu Lys Glu Asp Ser Lys Val Ile Pro Thr Glu Cys Ala
        275                 280                 285

Ile Lys Val Phe Lys Thr Thr Leu Asn Glu Phe Lys Asn Arg Asp Lys
        290                 295                 300

Tyr Ile Lys Asp Asp Phe Arg Phe Lys Asp Arg Phe Ser Lys Leu Asn
305                 310                 315                 320

Pro Arg Lys Ile Ile Arg Met Trp Ala Glu Lys Glu Met His Asn Leu
            325                 330                 335

Ala Arg Met Gln Arg Ala Gly Ile Pro Cys Pro Thr Val Val Leu Leu
            340                 345                 350

Lys Lys His Ile Leu Val Met Ser Phe Ile Gly His Asp Gln Val Pro
        355                 360                 365

Ala Pro Lys Leu Lys Glu Val Lys Leu Asn Ser Glu Glu Met Lys Glu
    370                 375                 380

Ala Tyr Tyr Gln Thr Leu His Leu Met Arg Gln Leu Tyr His Glu Cys
385                 390                 395                 400

Thr Leu Val His Ala Asp Leu Ser Glu Tyr Asn Met Leu Trp His Ala
            405                 410                 415

Gly Lys Val Trp Leu Ile Asp Val Ser Gln Ser Val Glu Pro Thr His
            420                 425                 430

Pro His Gly Leu Glu Phe Leu Phe Arg Asp Cys Arg Asn Val Ser Gln
        435                 440                 445

Lys Gly Gly Val Lys Glu Ala Leu Ser Glu Arg Glu Leu Phe Asn Ala
    450                 455                 460

Val Ser Gly Leu Asn Ile Thr Ala Asp Asn Glu Ala Asp Phe Leu Ala
465                 470                 475                 480

Glu Ile Glu Ala Leu Glu Lys Met Asn Glu Asp His Val Gln Lys Asn
            485                 490                 495

Gly Arg Lys Ala Ala Ser Phe Leu Lys Asp Asp Gly Asp Pro Pro Leu
            500                 505                 510

Leu Tyr Asp Glu
        515
```

COMPOSITIONS AND METHODS FOR TREATING BETA-GLOBINOPATHIES

RELATED APPLICATIONS

This application claims priority to U.S. Provisional Patent Application No. 62/756,497, filed Nov. 6, 2018, the contents of which are hereby incorporated by reference in the entirety for all purposes.

REFERENCE TO A SEQUENCE LISTING

The Sequence Listing written in file SequenceListing_077867-1162156-652100US.txt, created on Mar. 16, 2020, 15,771 bytes, machine format IBM-PC, MS-Windows operating system, is hereby incorporated by reference in its entirety for all purposes.

BACKGROUND OF THE INVENTION

Disorders of adult beta-globin (HBB) synthesis, or beta-globinopathies, are the most common monogenic disorders in the world. Two best-known examples include sickle cell disease and beta-thalassemia.

Sickle cell disease is caused by a single point mutation known as HbS in beta-globin, where a hydrophilic amino acid glutamic acid is substituted with a hydrophobic amino acid valine at the sixth position due to codon GAG being replaced by GTG. This substitution creates a hydrophobic spot on the outside of the protein, which tends to stick to the hydrophobic region of an adjacent hemoglobin molecule's beta chain. This further causes clumping of hemoglobin molecules into rigid fibers, causing "sickling" of the entire red blood cells in the HbS/HbS homozygotes. While the homozygous HbS/HbS alleles lead to a severe and potentially fatal genetic disorder, heterozygous HbS carriers are resistant to malaria and are minimally affected by the symptoms of anemia. Beta-thalassemia is a genetic disease caused by total or partial loss of beta-globin in a patient. Total loss, termed thalassemia major or beta-0-thalassemia, is due to mutation in both alleles of the beta-globin genes leading to failure to form beta chain of hemoglobin. It prevents oxygen supply in the tissues and can therefore be highly lethal. Symptoms, such as severe anemia and heart attack, often appear within two years after birth. Reduced beta-globin function termed thalassemia minor or beta+ thalassemia is due to mutation in only one of the alleles. It is less severe, but patients are prone to other diseases such as asthma and liver problems.

Beta-globinopathies can be treated by lifelong blood transfusion and bone marrow transplantation. Although previous studies have demonstrated the curative potential of bone marrow transplantation, this approach is limited to a small fraction of affected patients due to the requirement for an HLA-matched donor, the highly specialized approach that requires critical infrastructure, and the high cost. In a more recent study, transcription factor Pogo transposable element with Zinc finger domain (POGZ) has been shown to negatively regulate beta-globin synthesis, suggesting its suppression as a possible means for treating beta-globinopathies. Targeting a transcription factor, however, tends to present many practical difficulties in the context of developing therapeutic agents. Therefore, there exists a distinct need to develop new and cost-effective treatment methods, especially by increasing fetal hemoglobin expression as a potential cure for beta-globinopathies. This invention fulfills this and other related needs.

BRIEF SUMMARY OF THE INVENTION

The application provides the first disclosure of RIO kinase 3, a serine/threonine kinase and a member of the right open reading frame (RIO) kinase family, playing a role as a downstream effector of transcription factor Pogo transposable element with Zinc finger domain (POGZ) in the negative regulation of beta-globin synthesis. New compositions and methods for treating diseases and disorders involving suppressed beta-globin synthesis are therefore devised from this discovery.

As such, in a first aspect, this invention provides a method for promoting beta-globin synthesis in a cell. The method includes a step of contacting the cell with an effective amount of an inhibitor of RIOK3. In some embodiments, the cell is an erythroid cell, e.g., a primary erythroid progenitor cell or a CD34+ erythroid cell. In some embodiments, the cell is with the body of a patient, especially a human patient.

In some embodiments, the method comprises administering an effective amount of an inhibitor of RIOK3 to the patient. In some embodiments, the inhibitor is a neutralizing antibody against RIOK3 (e.g., a monoclonal or polyclonal antibody that specifically binds to RIOK3 protein and interferes with its activity), an siRNA, a microRNA, a miniRNA, a lncRNA, an antisense oligonucleotide, or a small molecule (e.g., Midostaurin, Axitinib, Bosutinib, or Ruxolitinib). In some embodiments, the inhibitor is administered by subcutaneous, intramuscular, intravenous, intraperitoneal, or oral administration. In some embodiments, the inhibitor is administered in the form of a solution, a powder, a paste, a tablet, or a capsule. In some embodiments, the patient receiving treatment by the claimed method has been diagnosed with a beta-globinopathy, such as sickle cell disease or beta-thalassemia. The patient optionally is receiving concurrently another therapy for the beta-globinopathy, such as blood transfusion.

In a second aspect, the present invention provides a composition comprising an effective amount of an inhibitor of RIOK3 and a physiologically acceptable excipient. In some embodiments, the composition is formulated for subcutaneous, intramuscular, intravenous, intraperitoneal, or oral administration. For example, the composition may be in form of a solution, a powder, a paste, a tablet, or a capsule. In some embodiments, the composition comprises one or more of the RIOK3 inhibitor. In some embodiments, the inhibitor is a neutralizing antibody against RIOK3 (e.g., a monoclonal or polyclonal antibody that specifically binds to RIOK3 protein and interferes with its activity), an siRNA, a microRNA, a miniRNA, a lncRNA, an antisense oligonucleotide, or a small molecule (e.g., Midostaurin, Axitinib, Bosutinib, or Ruxolitinib). In some embodiments, the inhibitor is Midostaurin, Axitinib, Bosutinib, or Ruxolitinib, or any combinations thereof.

In a third aspect, the present invention provides a kit for promoting beta-globin synthesis. The kit includes a container containing a composition comprising an effective amount of an inhibitor of RIOK3. Optionally, a second container containing a second RIOK3 inhibitor in an effective amount is also included in the kit. In some embodiments, the RIOK3 inhibitor-containing composition is formulated for subcutaneous, intramuscular, intravenous, intraperitoneal, topical, or oral administration. For example, the composition may be in form of a solution, a powder, a paste, a tablet, or a capsule. In some embodiments, the inhibitor is a neutralizing antibody against RIOK3 (e.g., a monoclonal or polyclonal antibody that specifically binds to RIOK3 protein and interferes with its activity), an siRNA, a microRNA, a miniRNA, a lncRNA, an antisense oligonucleotide, or a small molecule (e.g., Midostaurin, Axitinib, Bosutinib, or Ruxolitinib). In some embodiments, the inhibitor is Midostaurin, Axitinib, Bosutinib, or Ruxolitinib, or any combinations thereof. In some embodiments, the kit further comprises an instruction manual for administration of the composition comprising the RIOK3 inhibitor(s).

Related to this aspect of the present invention, a use of a RIOK3 inhibitor is further provided for the manufacturing of (1) a medicament for treating beta-globinopathies; or (2) a kit containing the medicament for treating beta-globinopathies. In some embodiments, the medicament comprising an effective amount of one or more RIOK3 inhibitors is formulated for subcutaneous, intramuscular, intravenous, intraperitoneal, topical, or oral administration. For example, the medicament may be in form of a solution, a powder, a paste, a tablet, or a capsule. In some embodiments, the inhibitor is a neutralizing antibody against RIOK3 (e.g., a monoclonal or polyclonal antibody that specifically binds to RIOK3 protein and interferes with its activity), an siRNA, a microRNA, a miniRNA, a lncRNA, an antisense oligonucleotide, or a small molecule (e.g., Midostaurin, Axitinib, Bosutinib, or Ruxolitinib). In some embodiments, the inhibitor used for manufacturing the medicament or kit for treating a beta-globinopathy is Midostaurin, Axitinib, Bosutinib, or Ruxolitinib, or any combinations thereof.

BRIEF DESCRIPTION OF THE DRAWINGS

FIG. 10: RIOK3 inhibitors: midostaurin, axitinib, bosutinib, and Ruxolitinib are FDA approved.

DEFINITIONS

Figure 1:
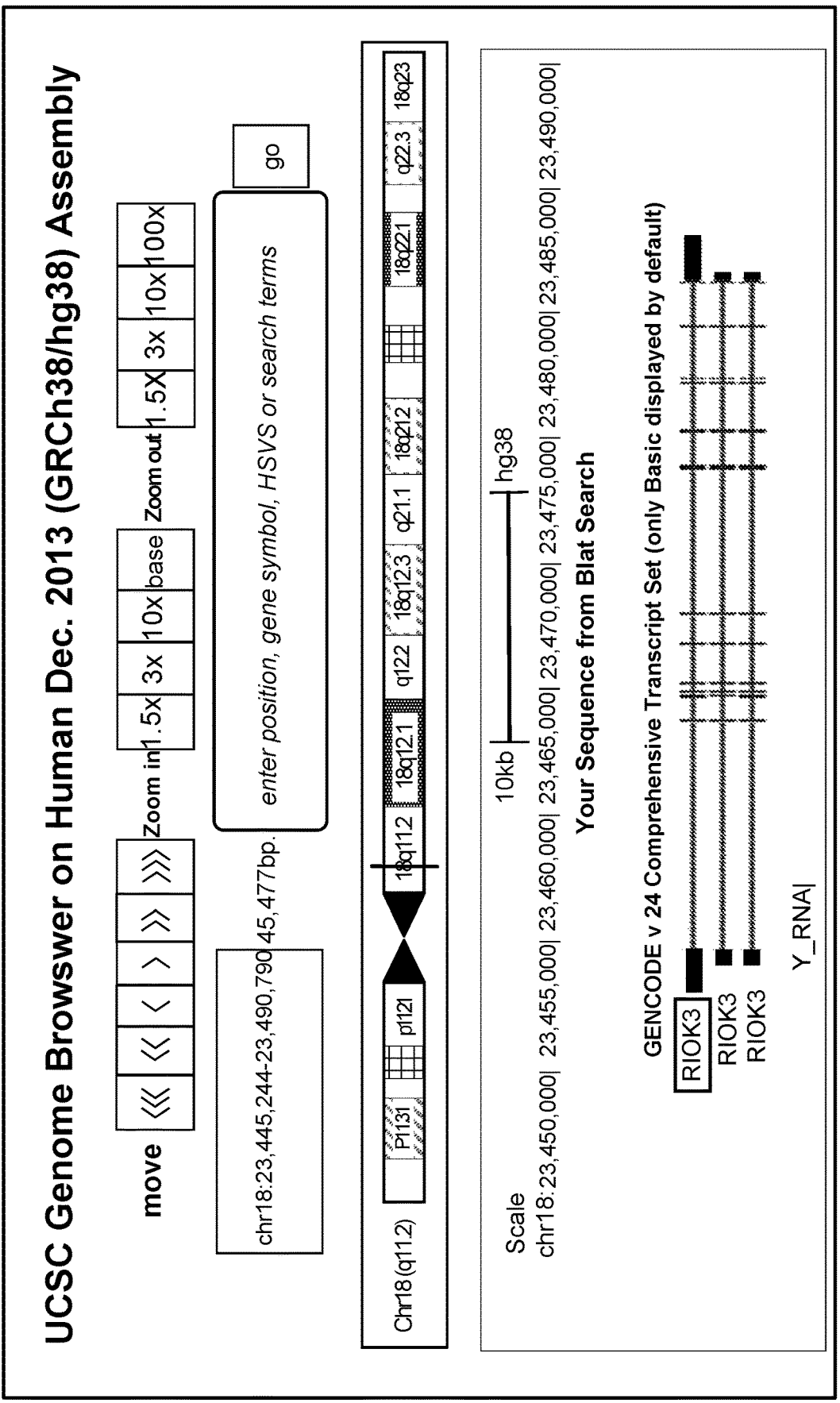
FIG. 1: Human RIO kinase 3 genomic location.

The term "RIO kinase 3" or "RIOK3" refers to a serine/threonine kinase belonging to the family of the right open reading frame (RIO) kinases. The human RIOK3 is encoded by the gene located on human chromosome 18 23,445,244-23,490,720 (45,477 bp), and its cDNA sequence is set forth in SEQ ID NO:1. As used herein, this term encompasses human RIOK3 as well as homologues or orthologues of this protein in other species with at least 80%, 85%, 90%, 95% or higher sequence homology and retaining the same or similar kinase activity. The term also includes all variants of the gene product (especially human RIOK3) due to alternative splicing. Exemplary human RIOK3 amino acid sequences are provided herein as SEQ ID NOs:2-4.

The term "beta-globinopathy" encompasses any disease or disorder that involves diminished beta-globin synthesis, including complete loss of beta-globin, in an individual. Beta-globinopathies include, but are not limited to, sickle cell disease and beta-thalassemia.

The term "erythroid cell" or "erythrocyte" refers to the blood cell type also known as the red blood cell (RBC). Erythrocytes are rich in hemoglobin, an iron-containing multiunit protein that is responsible for carrying oxygen in the bloodstream and delivering oxygen to cells and tissues throughout the body.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins, W. H. Freeman and Co., N. Y. (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

An "antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H$1 by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially an Fab with part of the hinge region (see, Paul (Ed.) *Fundamental Immunology*, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology.

Further modification of antibodies by recombinant technologies is also well known in the art. For instance, chimeric antibodies combine the antigen binding regions (variable regions) of an antibody from one animal with the constant regions of an antibody from another animal. Generally, the antigen binding regions are derived from a non-human animal, while the constant regions are drawn from human antibodies. The presence of the human constant regions reduces the likelihood that the antibody will be rejected as foreign by a human recipient. On the other hand, "humanized" antibodies combine an even smaller portion of the non-human antibody with human components. Generally, a humanized antibody comprises the hypervariable regions, or complementarity determining regions (CDR), of a non-human antibody grafted onto the appropriate framework regions of a human antibody. Antigen binding sites may be wild type or modified by one or more amino acid substitutions, e.g., modified to resemble human immunoglobulin more closely. Both chimeric and humanized antibodies are made using recombinant techniques, which are well-known in the art (see, e.g., Jones et al. (1986) *Nature* 321:522-525).

Thus, the term "antibody," as used herein, also includes antibody fragments either produced by the modification of whole antibodies or antibodies synthesized de novo using recombinant DNA methodologies (e.g., single chain Fv, a chimeric or humanized antibody).

The term "recombinant" when used with reference, e.g., to a cell, or a nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "promoter" is defined as an array of nucleic acid control sequences that direct transcription of a polynucleotide sequence. As used herein, a promoter includes necessary polynucleotide sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a polynucleotide expression control sequence (such as a promoter, or array of transcription factor binding sites) and a second polynucleotide sequence, wherein the expression control sequence directs transcription of the polynucleotide sequence corresponding to the second sequence.

An "expression cassette" is a nucleic acid construct, generated recombinantly or synthetically, with a series of specified polynucleotide elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter.

The term "heterologous" as used in the context of describing the relative location of two elements, refers to the two elements such as polynucleotide sequences (e.g., a promoter or a protein/polypeptide-encoding sequence) or polypeptide sequences (e.g., two peptides as fusion partners within a fusion protein) that are not naturally found in the same relative positions. Thus, a "heterologous promoter" of a gene refers to a promoter that is not naturally operably linked to that gene. Similarly, a "heterologous polypeptide" or "heterologous polynucleotide" to a particular protein or its encoding sequence is one derived from an origin that is different from that particular protein, or if derived from the same origin but not naturally connected to that particular protein or its coding sequence in the same fashion. The fusion of one polypeptide (or its coding sequence) with a heterologous polypeptide (or polynucleotide sequence) does not result in a longer polypeptide or polynucleotide sequence that can be found in nature.

A "label," "detectable label," or "detectable moiety" is a composition detectable by radiological, spectroscopic, photochemical, biochemical, immunochemical, chemical, or other physical means. For example, useful labels include radioisotopes such as $^{32}P$, fluorescent dyes, electron-dense reagents, enzymes (e.g., as commonly used in an ELISA), biotin, digoxigenin, or haptens and proteins that can be made detectable, e.g., by incorporating a radioactive component into a polypeptide or used to detect antibodies specifically reactive with the polypeptide. Typically a detectable label is a heterologous moiety attached to a probe or a molecule (e.g., a protein or nucleic acid) with defined binding characteristics (e.g., a polypeptide with a known binding specificity or a polynucleotide), so as to allow the presence of the probe/molecule (and therefore its binding target) to be readily detectable. The heterologous nature of the label ensures that it has an origin different from that of the probe or molecule that it labels, such that the probe/molecule attached with the detectable label does not constitute a naturally occurring composition (e.g., a naturally occurring polynucleotide or polypeptide sequence).

The phrase "specifically hybridize(s) to" refers to the binding, duplexing, or hybridization of one polynucleotide sequence to another polynucleotide sequence based on Watson-Crick nucleotide base-pairing under stringent hybridization conditions when that sequences are present in a complex mixture (e.g., total cellular or library DNA or RNA). The phrase "stringent hybridization conditions" refers to conditions under which a nucleic acid (e.g., a polynucleotide probe) will hybridize to its target nucleotide sequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency hybridization conditions include: 50% formamide, 5×SSC and 1% SDS incubated at 42° C. or 5×SSC and 1% SDS incubated at 65° C., with a wash in 0.2×SSC and 0.1% SDS at 65° C.

The term "immunoassay" describes an assay that uses an antibody to specifically bind an antigen. The immunoassay is characterized by the use of specific binding properties of a particular antibody to identify, isolate, target, and/or detect the presence or quantity of the antigen.

The phrase "specifically binds," when used to describe the binding relationship between an antibody and its target antigen, refers to a binding reaction that is determinative of the presence of the antigen (e.g., a polypeptide) in a heterogeneous population of proteins and other biologics. Thus, under designated immunoassay conditions, the specified antibodies bind to a particular polypeptide at least two times the background and do not substantially bind in a significant amount to other polypeptides or other antigens present in the sample. Specific binding to an antibody under such conditions may require an antibody that is selected for its specificity for a particular protein. For example, polyclonal antibodies raised to a RIOK3 having the amino acid sequence of SEQ ID NO:1, can be selected to obtain only those polyclonal antibodies that are specifically immunoreactive with that specific protein and not with other proteins, e.g., other members of the RIO kinase family. This selection may be achieved by subtracting out antibodies that cross-react with molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically, a specific binding reaction will yield at least twice of the background signal or noise and more typically more than 5, 10, 20, 50, or up to 100 times the background.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, e.g., cultured cells, explants, and cells in vivo.

The term "inhibiting" or "inhibition," as used herein, refers to any detectable negative effect on a target biological process, such as protein phosphorylation, cellular signal transduction, protein synthesis, cell proliferation, tumorigenicity, and metastatic potential etc. Typically, an inhibition is reflected in a decrease of at least 10%, 20%, 30%, 40%, or 50% in target process (e.g., RIOK3-mediated MDA5 phosphorylation), or any one of the downstream parameters mentioned above, when compared to a control. In a similar fashion, the term "increasing" or "increase" is used to describe any detectable positive effect on a target biological process, for example, beta-globin synthesis in an erythroid, such as a positive change of at least 25%, 50%, 75%, 100%, or as high as 2, 3, 4, 5 or up to 10 or 20 fold, when compared to a control.

The term "effective amount," as used herein, refers to an amount that is sufficient to produces an intended effect for which a substance is administered. The effect may include a desirable change in a biological process (e.g., increased beta-globin synthesis) as well as the prevention, correction, or inhibition of progression of the symptoms of a disease/condition and related complications to any detectable extent. The exact amount "effective" for achieving a desired effect will depend on the nature of the therapeutic agent, the manner of administration, and the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

The term "about" denotes a range of +/−10% of a predetermined value. For example, "about 10" sets a range of 90% to 110% of 10, i.e., 9 to 11.

DETAILED DESCRIPTION OF THE INVENTION

I. Introduction

In their earlier studies the present inventors identified the potential transcription factor C2H2 zinc finger protein POGZ as a negative regulator of mouse embryonic β-like globin and human fetal hemoglobin expression. Downregulation of POGZ was shown to increase beta-globin expression, making a POGZ a potential target for treating beta-globinopathies. See, e.g., Gudmundsdottir et al. 2018, *Cell Reports* 23:3236-3248. The inventors have now discovered as a downstream effector of POGZ, Rio Kinase 3 (RIOK3), and have demonstrated that the suppression of RIOK3 leads to a significant increase in beta-globin expression.

While RIOK3 has been previously reported to have a role in innate immune response, mouse erythroblast enucleation, and cancer cell invasion and metastasis (see, e.g., Takashima et al., *Cell Rep.* 2015 Apr. 14; 11(2):192-200; Zhang et al., *Genes Dev.* 2011 Jan. 15; 25(2):119-24; Singleton et al., *Oncogene* 2015 Sep. 3; 34(36):4713-22), this disclosure is the first to illustrate its involvement in beta-globin synthesis. Given that RIOK3 as a kinase is easier to target for regulation of beta-globin synthesis than to target a transcription factor such as POGZ, this disclosure provides new and more effective therapeutic methods for the treatment and potential cure of beta-globinopathies such as sickle cell disease and beta-thalassemia.

II. General Recombinant Technology

Basic texts disclosing general methods and techniques in the field of recombinant genetics include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The sequence of a gene of interest, a polynucleotide encoding a polypeptide of interest, and synthetic oligonucleotides can be verified after cloning or subcloning using, e.g., the chain termination method for sequencing double-stranded templates of Wallace et al., *Gene* 16: 21-26 (1981).

II. RIOK3 Inhibitors

Earlier work by the present inventors illustrated the involvement of pogo transposable element with zinc-finger domain (POGZ), a zinc-finger protein and proposed transcription factor, in the suppression of embryonic globin gene expression in erythroid cells. Their latest discovery reveals that serine/threonine kinase RIOK3 is a downstream kinase in the signal pathway mediated by POGZ in the negative regulation of beta-globin synthesis, and that beta-globin synthesis is significantly increased when RIOK3 expression or activity is suppressed or abolished. This understanding leads to the use of RIOK3 inhibitors, which may act at the level of RIOK3 gene expression or at the level of RIOK3 protein enzymatic activity, for treating diseases and disorders caused by abolished or severely diminished beta-globin synthesis. Various categories of possible RIOK3 inhibitors acting through different mechanisms are useful and discussed below.

A. RIOK3 Antibodies

Polyclonal or monoclonal antibodies against the RIOK3 protein can potentially serve as inhibitors of RIOK3 enzymatic activity by way of directly and specifically binding the kinase to interfere with its interaction with its substrate and/or co-factor(s), thus inhibiting RIOK3 activity.

Methods for producing polyclonal and monoclonal antibodies that react specifically with an immunogen of interest are known to those of skill in the art (see, e.g., Coligan, *Current Protocols in Immunology* Wiley/Greene, NY, 1991; Harlow and Lane, *Antibodies: A Laboratory Manual* Cold Spring Harbor Press, NY, 1989; Stites et al. (eds.) *Basic and Clinical Immunology* (4th ed.) Lange Medical Publications, Los Altos, Calif., and references cited therein; Goding, *Monoclonal Antibodies: Principles and Practice* (2d ed.) Academic Press, New York, N.Y., 1986; and Kohler and Milstein *Nature* 256: 495-497, 1975). Such techniques include antibody preparation by selection of antibodies from libraries of recombinant antibodies in phage or similar vectors (see, Huse et al., *Science* 246: 1275-1281, 1989; and Ward et al., *Nature* 341: 544-546, 1989).

In order to produce antisera containing antibodies with desired specificity, the polypeptide of interest (e.g., an RIOK3 protein) or an antigenic fragment thereof can be used to immunize suitable animals, e.g., mice, rabbits, or primates. A standard adjuvant, such as Freund's adjuvant, can be used in accordance with a standard immunization protocol. Alternatively, a synthetic antigenic peptide derived from that particular polypeptide can be conjugated to a carrier protein and subsequently used as an immunogen.

The animal's immune response to the immunogen preparation is monitored by taking test bleeds and determining the titer of reactivity to the antigen of interest. When appropriately high titers of antibody to the antigen are obtained, blood is collected from the animal and antisera are prepared. Further fractionation of the antisera to enrich antibodies specifically reactive to the antigen and purification of the antibodies can be performed subsequently, see, Harlow and Lane, supra, and the general descriptions of protein purification provided above.

Monoclonal antibodies are obtained using various techniques familiar to those of skill in the art. Typically, spleen cells from an animal immunized with a desired antigen are immortalized, commonly by fusion with a myeloma cell (see, Kohler and Milstein, *Eur. J. Immunol.* 6:511-519, 1976). Alternative methods of immortalization include, e.g., transformation with Epstein Barr Virus, oncogenes, or retroviruses, or other methods well known in the art. Colonies arising from single immortalized cells are screened for production of antibodies of the desired specificity and affinity for the antigen, and the yield of the monoclonal antibodies produced by such cells may be enhanced by various techniques, including injection into the peritoneal cavity of a vertebrate host.

Additionally, monoclonal antibodies may also be recombinantly produced upon identification of nucleic acid sequences encoding an antibody with desired specificity or a binding fragment of such antibody by screening a human B cell cDNA library according to the general protocol outlined by Huse et al., supra. The general principles and methods of recombinant polypeptide production discussed above are applicable for antibody production by recombinant methods.

B. Antisense Oligonucleotides

In some embodiments, the inhibitor is an antisense oligonucleotide. Antisense oligonucleotides are relatively short nucleic acids that are complementary (or antisense) to the coding strand (sense strand) of the mRNA encoding RIOK3. Although antisense oligonucleotides are typically RNA based, they can also be DNA based. Also, antisense oligonucleotides are often modified to increase their stability.

Without being bound by theory, the binding of these relatively short oligonucleotides to the mRNA is believed to induce stretches of double stranded RNA that trigger degradation of the messages by endogenous RNAses. Additionally, sometimes the oligonucleotides are specifically designed to bind near the promoter of the coding sequence, and under these circumstances, the antisense oligonucleotides may additionally interfere with translation of the mRNA. Regardless of the specific mechanism by which antisense oligonucleotides function, their administration to a cell or tissue allows the degradation of the mRNA encoding RIOK3. Accordingly, antisense oligonucleotides decrease the expression and/or activity of RIOK3.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al., 1989, *Proc. Natl. Acad. Sci.* U.S.A. 86:6553-6556; Lemaitre et al., 1987, *Proc. Natl. Acad. Sci.* 84:648-652; WO 88/09810) or the blood-brain barrier (see, e.g., WO 89/10134), hybridization-triggered cleavage agents (See, e.g., Krol et al., 1988, *BioTechniques* 6:958-976) or intercalating agents (see, e.g., Zon, 1988, *Pharm. Res.* 5:539-549). To this end, the oligonucleotide can be conjugated to another molecule.

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, *Nucl. Acids Res.* 16:3209), methylphosphonate oligonucleotides can be prepared by use of controlled pore glass polymer supports (Sarin et al., 1988, *Proc. Natl. Acad. Sci.* U.S.A. 85:7448-7451) etc.

A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

It may be difficult to achieve intracellular concentrations of the antisense sufficient to suppress translation on endogenous mRNAs in certain instances. Therefore, another approach utilizes a recombinant DNA construct in which the antisense oligonucleotide is placed under the control of a strong pol III or pol II promoter. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, *Nature* 290:304-310), the promoter contained in the 3' long terminal repeat of Rous sarcoma virus (Yamamoto et al., 1980, *Cell* 22:787-797), the herpes thymidine kinase promoter (Wagner et al., 1981, *Proc. Natl. Acad. Sci.* U.S.A. 78:1441-1445), the regulatory sequences of the metallothionein gene (Brinster et al., 1982, *Nature* 296:39-42), etc. Any type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

C. Small Interfering RNA

In some embodiments, the inhibitor is a small interfering RNA (siRNA or RNAi) molecule. RNAi constructs comprise double stranded RNA that can specifically block expression of a target gene. "RNA interference" or "RNAi" is a term initially applied to a phenomenon where double-stranded RNA (dsRNA) blocks gene expression in a specific and post-transcriptional manner. RNAi provides a useful method of inhibiting gene expression in vitro or in vivo. RNAi constructs can include small interfering RNAs (siRNAs), short hairpin RNAs (shRNAs), and other RNA species that can be cleaved in vivo to form siRNAs. RNAi constructs herein also include expression vectors ("RNAi expression vectors") capable of giving rise to transcripts which form dsRNAs or hairpin RNAs in cells, and/or transcripts which can produce siRNAs in vivo.

RNAi expression vectors express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA, which can be processed to an siRNA), and (3) appropriate transcription initiation and termination sequences. The choice of promoter and other regulatory elements generally varies according to the intended host cell.

The RNAi constructs contain a nucleotide sequence that hybridizes under physiologic conditions of the cell to the nucleotide sequence of at least a portion of the mRNA transcript for the gene to be inhibited (i.e., a RIOK3-encoding polynucleotide sequence). The double-stranded RNA need only be sufficiently similar to natural RNA that it has the ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of an nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, any modified ribonucleotide can be introduced by in vitro enzymatic or organic synthesis.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

In certain embodiments, the RNAi construct is in the form of a short hairpin structure (named as shRNA). The shRNAs can be synthesized exogenously or can be formed by transcribing from RNA polymerase III promoters in vivo. Examples of making and using such hairpin RNAs for gene silencing in mammalian cells are described in, for example, Paddison et al., *Genes Dev,* 2002, 16:948-58; McCaffrey et al., *Nature,* 2002, 418:38-9; Yu et al., *Proc Natl Acad Sci USA,* 2002, 99:6047-52). Often, such shRNAs are engineered in cells or in an animal to ensure continuous and stable suppression of a desired gene. It is known in the art that siRNAs can be produced by processing a hairpin RNA in the cell.

A plasmid can be used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

D. Ribozymes

In some embodiments, the RIOK3 inhibitor is a ribozyme. Ribozymes molecules designed to catalytically cleave an mRNA transcripts can also be used to prevent translation of mRNA (See, e.g., WO 90/11364; Sarver et al., 1990, *Science* 247:1222-1225 and U.S. Pat. No. 5,093,246). While ribozymes that cleave mRNA at site-specific recognition sequences can be used to destroy particular mRNAs, the use of hammerhead ribozymes is preferred.

Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, *Nature*, 334:585-591.

The ribozyme inhibitors of this invention also include RNA endoribonucleases (hereinafter "Cech-type ribozymes") such as the one that occurs naturally in Tetrahymena thermophila (known as the IVS, or L-19 IVS RNA) and has been extensively described by Thomas Cech and collaborators (Zaug, et al., 1984, *Science*, 224:574-578; Zaug and Cech, 1986, *Science*, 231:470-475; Zaug, et al., 1986, *Nature*, 324:429-433; WO 88/04300; Been and Cech, 1986, *Cell*, 47:207-216). The Cech-type ribozymes have an 8-basepair active site that hybridizes to a target RNA sequence whereafter cleavage of the target RNA takes place. The invention encompasses those Cech-type ribozymes that target 8-basepair active site sequences.

As in the antisense approach, the ribozymes can be composed of modified oligonucleotides (e.g., for improved stability, targeting, etc.) and can be delivered to cells in vitro or in vivo. A preferred method of delivery involves using a DNA construct "encoding" the ribozyme under the control of a strong constitutive pol III or pol II promoter, so that transfected cells will produce sufficient quantities of the ribozyme to destroy targeted messages and inhibit translation. Because ribozymes unlike antisense molecules, are catalytic, a lower intracellular concentration is required for efficiency.

There are currently two basic types of DNA enzymes, and both of these were identified by Santoro and Joyce (see, e.g., U.S. Pat. No. 6,110,462). The 10-23 DNA enzyme comprises a loop structure which connect two arms. The two arms provide specificity by recognizing the particular target nucleic acid sequence while the loop structure provides catalytic function under physiological conditions.

Briefly, to design an ideal DNA enzyme that specifically recognizes and cleaves a target nucleic acid, one of skill in the art must first identify the unique target sequence. This can be done using the same approach as outlined for antisense oligonucleotides. Preferably, the unique or substantially sequence is a G/C rich of approximately 18 to 22 nucleotides. High G/C content helps insure a stronger interaction between the DNA enzyme and the target sequence.

When synthesizing the DNA enzyme, the specific antisense recognition sequence that will target the enzyme to the message is divided so that it comprises the two arms of the DNA enzyme, and the DNA enzyme loop is placed between the two specific arms.

Methods of making and administering DNA enzymes can be found, for example, in U.S. Pat. No. 6,110,462. Similarly, methods of delivery DNA ribozymes in vitro or in vivo include methods of delivery RNA ribozyme, as outlined in detail above. Additionally, one of skill in the art will recognize that, like antisense oligonucleotide, DNA enzymes can be optionally modified to improve stability and improve resistance to degradation.

E. Gene Editing

The inhibition of RIOK3-mediated cellular signaling by suppression of RIOK3 expression and/or enzymatic activity can be achieved by way of disruption of the genetic sequence encoding the RIOK3 protein. One effective means of targeted gene cleavage is the CRISPR system.

The term CRISPR, abbreviation for Clustered Regularly Interspaced Short Palindromic Repeats, was originally coined in reference to segments of prokaryotic DNA that contain short, repetitive base sequences, initially found in bacteria and archaea. In a palindromic repeat, the sequence of nucleotides is the same in both directions. Each repetition is followed by short segments of spacer DNA from previous exposures to foreign DNA (e.g., DNA of a virus). Small clusters of Cas (CRISPR-associated) genes are located next to CRISPR sequences. It was later recognized that the CRISPR/Cas system is a prokaryotic immune system that confers resistance to foreign genetic elements especially those of viral origin and thereby provides a form of acquired immunity. RNA harboring the spacer sequence helps Cas (CRISPR-associated) proteins recognize and cut exogenous DNA. Other RNA-guided Cas proteins cut foreign RNA. CRISPRs are found in approximately 50% of sequenced bacterial genomes and nearly 90% of sequenced archaea, and recently the CRISPR/Cas system have been adapted for use in targeted gene editing in eukaryotic cells. See, e.g., Ledford (2016), *Nature* 531 (7593):156-9.

A simple version of the CRISPR/Cas system, CRISPR/Cas9, has been modified to edit genomes. By delivering the Cas9 nuclease complexed with a synthetic guide RNA (gRNA) into a cell, typically by transfecting the cell with one or more expression vectors encoding for the Cas9 nuclease and the gRNA, the cell's genome can be cut at a pre-selected location, allowing a target gene (e.g., the RIOK3 gene) to be removed and/or substituted by a new coding sequence.

In the instant case, an expression vector (for example, a viral vector) carrying the coding sequence for a RIOK3-specific gRNA can be introduced into a cell in which the endogenous RIOK3 gene is to be knocked out (for example, an erythroid cell or an erythroid progenitor cell). The same expression vector optionally also carries the coding sequence for the CRISPR/Cas9 nuclease or equivalent. In the alternative, a separate expression vector may be used to introduce the CRISPR/Cas9 nuclease coding sequence for its expression in the target cells. In some cases, more than one (e.g., two) distinct gRNAs are used to ensure removal and/or replacement of a target genomic sequence (e.g., one that encodes the RIOK3 protein).

F. Small Molecules

Chemical library of small molecules, especially those with known kinase inhibitory activity, can be screened to identify possible RIOK3 inhibitors. FIG. 10 shows some examples of such small molecule compounds that the present inventors have screened for the purpose of identifying RIOK3 inhibitors. From a collection of 72 inhibitors against 456 human kinases, midostaurin, axitinib, bosutinib, and ruxolitinib are among those that have been shown to inhibit RIOK3 kinase activity and also received FDA approval of human use. Midostaurin is an analogue of staurosporine and was originally described as a PKC inhibitor. It was later reported as an inhibitor of fms-related tyrosine kinase 3 (FLT3). It received FDA approval in 2017. Axitinib is a Type-1 kinase inhibitor, known to inhibit several receptor tyrosine kinases including VEGFR-1, VEGFR-2, VEGFR-3, platelet derived growth factor receptor (PDGFR), and cKIT. It received FDA approval in 2012. Bosutinib is a Type-1 kinase inhibitor and a dual inhibitor of Src family kinases and Abl kinase activity. It received FDA approval in 2012. Ruxolitinib is a Type-1 kinase inhibitor and was first approved by the US FDA in 2011. Ruxolitinib has high potency against Janus kinases 1 and 2 (JAK1, JAK2), as well as against the related family member, tyrosine kinase 2 (TYK2). Inhibitory activity against JAK3 is only slightly reduced compared to the other three family kinases. Marketed formulations may contain ruxolitinib phosphate. Following a similar approach additional small molecule inhibitors can be identified.

Thus, the present invention provides potential RIOK3 inhibitors having the general structures described below:

First, the inhibitor may be a compound having the structure shown in Formula I:

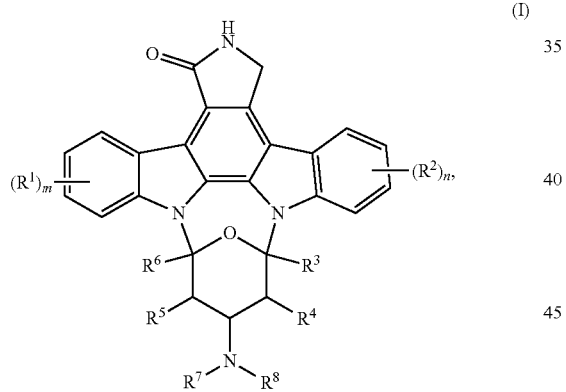

(I)

wherein:
each $R^1$ and $R^2$ are independently selected from the group consisting of halo, substituted or unsubstituted $C_{1-6}$ alkyl, substituted or unsubstituted $C_{1-6}$ alkenyl, substituted or unsubstituted alkoxy, acyl, acylamino, aminocarbonyl, aminosulfonyl, amino, substituted amino, substituted or unsubstituted aryl, substituted or unsubstituted carboxy, carboxyl esters, cyano, substituted or unsubstituted cycloalkyl, substituted or unsubstituted heteroaryl, substituted or unsubstituted heterocyclyl, hydroxyl, sulfonyl, substituted sulfonyl, thiol, thioalkyl;
each $R^3$, $R^4$, $R^5$, and $R^6$ are independently selected from the group consisting of hydrogen, halo, substituted or unsubstituted $C_{1-6}$ alkyl, substituted or unsubstituted $C_{1-6}$ alkenyl, substituted or unsubstituted alkoxy, acyl, acylamino, aminocarbonyl, aminosulfonyl, amino, substituted amino, substituted or unsubstituted aryl, substituted or unsubstituted carboxy, carboxyl esters, cyano, substituted or unsubstituted cycloalkyl, substituted or unsubstituted heteroaryl, substituted or unsubstituted heterocyclyl, hydroxyl, sulfonyl, substituted sulfonyl, thiol, thioalkyl;
each $R^7$ and $R^8$ are independently selected from the group consisting of hydrogen, substituted or unsubstituted $C_{3-8}$ cycloalkyl, substituted or unsubstituted $C_{1-8}$ alkyl, substituted or unsubstituted $C_{3-12}$ heterocyclyl, substituted or unsubstituted $C_{6-10}$ aryl, substituted or unsubstituted $C_{5-12}$ heteroaryl, acyl, substituted or unsubstituted carboxy, substituted or unsubstituted carboxyalkyl, and substituted or unsubstituted aryl; and
subscripts m and n are independently selected from 0, 1, 2, 3, or 4.

In one particular embodiment, the inhibitor is Midostaurin:

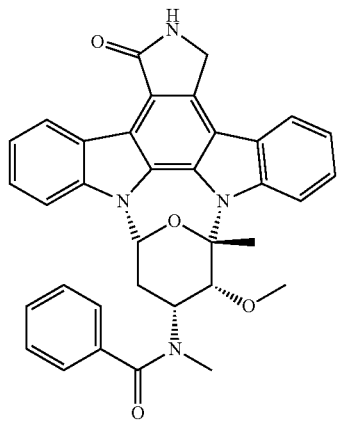

Second, the inhibitor may be a compound having the structure shown in Formula II:

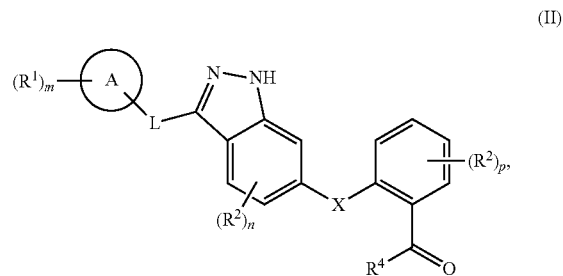

(II)

wherein:
A is an arylene or heteroarylene having 1 to 3 heteroatoms;
L is selected from the group consisting of a bond, substituted or unsubstituted $C_{1-6}$ alkylene, and substituted or unsubstituted $C_{1-6}$ alkenylene;
X is selected from the group consisting of —O—, —S—, —SO—, —S(O)$_2$—, and —NR$^5$—, wherein $R^5$ is selected from the group consisting of hydrogen, substituted or unsubstituted $C_{1-6}$ alkyl, substituted or unsubstituted aryl, substituted or unsubstituted heteroaryl, and substituted or unsubstituted heterocycloalkyl;
each $R^1$, $R^2$, and $R^3$ are independently selected from the group consisting of halo, substituted or unsubstituted $C_{1-6}$ alkyl, substituted or unsubstituted $C_{1-6}$ alkenyl, substituted or unsubstituted alkoxy, acyl, acylamino, aminocarbonyl, aminosulfonyl, amino, substituted amino, substituted or unsubstituted aryl, carboxyl, carboxyl esters, cyano, substituted or unsubstituted cycloalkyl, substituted or unsubstituted heteroaryl, substituted or unsubstituted heterocyclyl, hydroxyl, sulfonyl, substituted sulfonyl, thiol, thioalkyl;

$R^4$ is selected from the group consisting of —OH, —O—$C_{1-8}$ alkyl, —N($R^6$)$_2$, substituted or unsubstituted $C_{3-8}$ cycloalkyl, substituted or unsubstituted $C_{1-8}$ alkyl, substituted or unsubstituted $C_{3-12}$ heterocyclyl, substituted or unsubstituted $C_{6-10}$ aryl, and substituted or unsubstituted $C_{5-12}$ heteroaryl;

each $R^6$ is independently selected from hydrogen and $C_{1-6}$ alkyl; and subscripts m, n and p are independently selected from 0, 1, 2, or 3.

In one particular embodiment, the inhibitor is Axitinib:

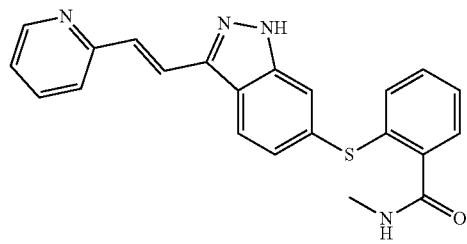 [SMILES: CNC(=O)c1ccccc1Sc1ccc2c(/C=C/c3ccccn3)n[nH]c2c1]

Third, the inhibitor may be a compound having the structure shown in Formula III:

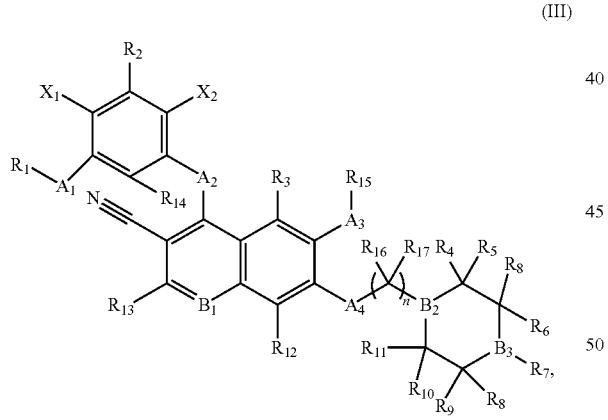

(III)

wherein
  $A_1$-$A_4$ are independently selected from carbon, nitrogen, oxygen, and sulfur;
  $B_1$-$B_4$ are independently selected from carbon and nitrogen;
  N is nitrogen;
  $R_1$-$R_{17}$ are independently selected from hydrogen, alkyl, or halogen;
  $X_1$-$X_4$ are independently selected from hydrogen, alkyl, or halogen; and
  n is from 1-30.

In one particular embodiment, the inhibitor is Bosutinib:

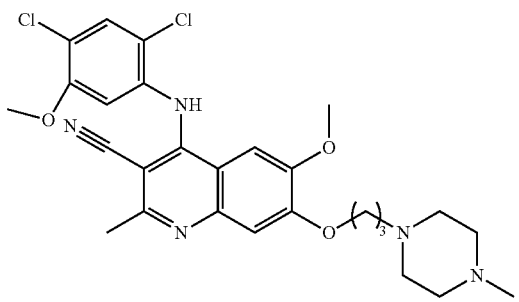

Fourth, the inhibitor may be a compound having the structure shown in Formula IV:

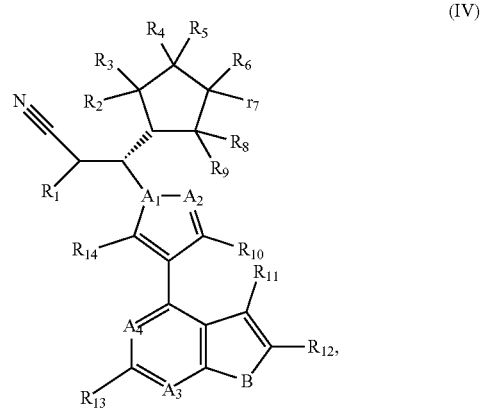

(IV)

wherein
  $A_1$-$A_4$ are independently selected from carbon, nitrogen, oxygen, and sulfur;
  B is carbon or nitrogen;
  N is nitrogen; and
  $R_1$-$R_{17}$ are independently selected from hydrogen, alkyl, or halogen.

In one particular embodiment, the inhibitor is Ruxolitinib:

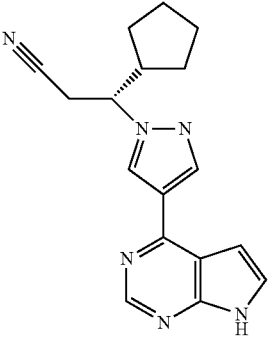

III. Identification of RIOK3 Inhibitors

Inhibitors of RIOK3 expression or activity can be of virtually any chemical and structural nature: they may be polypeptides, polynucleotides, and small molecules. As long as they possess confirmed inhibitory effect against RIOK3 as a downstream signal transduction mediator of POGZ, such inhibitors may be useful for promoting beta-globin synthesis and therefore useful for treating beta-globinopathies.

A. RIOK3 Binding Assays

An in vitro assay can be used to screen for potential inhibitors of RIOK3 signaling based in the direct binding between RIOK3 and a candidate compound. Once a compound is identified in the binding assay, further testing may be conducted to confirm and verify the compounds capability to inhibiting RIOK3-mediated signaling. In general, such an assay can be performed in the presence of an RIOK3 protein or a fragment thereof, for example, a recombinantly produced RIOK3 protein or fragment or a fusion protein of RIOK3 and a fusion partner (a heterologous polypeptide), under conditions permitting RIOK3 binding to a potential binding partner. For convenience, the RIOK3 protein or the candidate compound may be immobilized onto a solid support and/or labeled with a detectable moiety. A third molecule, such as an antibody (which may include a detectable label) to the RIOK3 protein, can also be used to facilitate detection.

In some cases, the binding assays can be performed in a cell-free environment; whereas in other cases, the binding assays can be performed within a cell or on the cell surface, for example, using cells recombinantly or endogenously expressing an appropriate RIOK3 protein or fusion polypeptide.

B. RIOK3 Functional Assays

The inhibitors of RIOK3-mediated cellular signaling are useful for their ability to negate the downstream effects of RIOK3 signaling, especially as anti-beta-globinopathy therapeutics for patients suffering from diseases or conditions involving lost or insufficient beta-globin synthesis. Assays for confirming such inhibitory effect of an inhibitor can be performed in vitro or in vivo. An in vitro assay typically involves exposure of cultured cells to an inhibitor and monitoring of subsequent biological and biochemical changes in the cells. For example, following exposure to an inhibitor at an adequate concentration for an appropriate amount of time, suitable cells (such as those capable of expressing beta-globin, e.g., erythroid cells or their progenitor cells) are examined for any potential changes in their beta-globin synthesis rate by immunoassays such as Western blot and in situ immunostaining, etc. Further downstream changes due to RIOK3 signaling, e.g., phosphorylation of the MIDA5 protein and expression of BCL11A protein, and expression of LRF expression can also be monitored to provide an indication of suppressed signaling via RIOK3. An inhibitory effect is detected when a decrease in RIOK3-mediated signaling, as indicated by any one aforementioned parameter, by at least 10%, 20%, 30%, 40%, 50%, 60%, 70%, 80%, 90% or more is observed.

The enhancing effects on the beta-globin synthesis by a RIOK3 inhibitor of the present invention can also be demonstrated in in vivo assays. For example, a RIOK3 inhibitor can be injected into animals that suffer from a beta-globinopathy (e.g., sickle cell disease or beta-thalassemia) and therefore show inadequate beta-globin expression and/or activity. Injection methods can be subcutaneous, intramuscular, intravenous, intraperitoneal in nature. Changes in disease development is subsequently monitored by various means, such as measuring the level of hemoglobin or number of red blood cells in the circulatory system, in comparison with a control group of animals with similar disease or condition but not given the inhibitor. The Examples section of this disclosure provides detailed description of some exemplary in vivo assays. An inhibitory effect is detected when a positive effect on hemoglobin level or RBC number is established in the test group. Preferably, the positive effect is at least a 10% increase; more preferably, the increase is at least 20%, 30%, 40%, 50%, 60%, 70%, 80%, 90%, 100%, 200%, or higher.

As stated above, RIOK3 inhibitors can have diverse chemical and structural features. For instance, an inhibitor can be a non-functional RIOK3 mutant that retaining the binding ability RIOK3 to its upstream or downstream signaling molecules, a neutralizing antibody to RIOK3 that interferes with RIOK3-mediated signaling, or any small molecule or macromolecule that simply hinders the interaction between RIOK3 and its upstream or downstream signaling molecules. Essentially any chemical compound can be tested as a potential inhibitor of RIOK3 signaling. Most preferred are generally compounds that can be dissolved in aqueous or organic (especially DMSO-based) solutions. Inhibitors can be identified by screening a combinatorial library containing a large number of potentially effective compounds. Such combinatorial chemical libraries can be screened in one or more assays, as described herein, to identify those library members (particular chemical species or subclasses) that display a desired characteristic activity. The compounds thus identified can serve as conventional "lead compounds" or can themselves be used as potential or actual therapeutics.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)) and carbohydrate libraries (see, e.g., Liang et al., *Science*, 274:1520-1522 (1996) and U.S. Pat. No. 5,593,853). Other chemistries for generating chemical diversity libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with β-D-glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see, Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and benzodiazepines, U.S. Pat. No. 5,288,514).

IV. Pharmaceutical Compositions and Administration

The present invention also provides pharmaceutical compositions or physiological compositions comprising an effective amount of a compound that inhibits RIOK3-mediated signaling and therefore promote beta-globin synthesis, such as a dominant negative RIOK3 mutant or its encoding nucleic acid, a nucleic acid encoding an antisense or miRNA, miniRNA, long non-coding RNA targeting RIOK3, an inactivating anti-RIOK3 antibody, small chemicals, peptides, proteins, natural extract compounds from herbs, or the like, in both prophylactic and therapeutic applications. Such pharmaceutical or physiological compositions also include one or more pharmaceutically or physiologically acceptable excipients or carriers. Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985). For a brief review of methods for drug delivery, see, Langer, *Science* 249: 1527-1533 (1990).

The pharmaceutical compositions of the present invention can be administered by various routes, e.g., oral, subcutaneous, transdermal, intramuscular, intravenous, or intraperitoneal. The preferred routes of administering the pharmaceutical compositions are local delivery to a relevant organ or tissue in a patient suffering from a condition involving suppressed or abolished beta-globin synthesis at daily doses of about 0.01-2500 mg, preferably 2.5-500 mg, of a RIOK3 inhibitor for a 70 kg adult human per day. The appropriate dose may be administered in a single daily dose or as divided doses presented at appropriate intervals, for example as two, three, four, or more subdoses per day.

For preparing pharmaceutical compositions containing a RIOK3 inhibitor such as midostaurin, axitinib, bosutinib, or ruxolitinib, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., midostaurin, axitinib, bosutinib, or ruxolitinib. In tablets, the active ingredient (an inhibitor of RIOK3 signaling) is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient of an inhibitor of RIOK3-mediated signaling. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active compound of a RIOK3 inhibitor with encapsulating material as a carrier providing a capsule in which the inhibitor (with or without other carriers) is surrounded by the carrier, such that the carrier is thus in association with the compound. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., a RIOK3 inhibitor such as midostaurin, axitinib, bosutinib, or ruxolitinib) or sterile solutions of the active component in solvents comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., a RIOK3 signaling inhibitor) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9, and most preferably from 7 to 8.

The pharmaceutical compositions containing a RIOK3 inhibitor can be administered for prophylactic and/or therapeutic treatments. In therapeutic applications, compositions are administered to a patient already suffering from a condition that involves insufficient beta-globin synthesis in an amount sufficient to prevent, cure, reverse, or at least partially slow or arrest the symptoms of the condition and its complications, such as the onset, progression, duration, and severity of the disease. An amount adequate to accomplish this is defined as a "therapeutically effective dose." Amounts effective for this use will depend on the severity of the disease or condition and the weight and general state of the patient, but generally range from about 0.1 mg to about 2,500 mg of the inhibitor per day for a 70 kg patient, with dosages of from about 2.5 mg to about 500 mg of the inhibitor per day for a 70 kg patient being more commonly used.

In prophylactic applications, pharmaceutical compositions containing a RIOK3 inhibitor are administered to a patient susceptible to or otherwise at risk of developing a disease or condition in which RIOK3-mediated signaling is undesirable, in an amount sufficient to delay or prevent the onset of the symptoms. Such an amount is defined to be a "prophylactically effective dose." In this use, the precise amounts of the inhibitor again depend on the patient's state of health and weight, but generally range from about 0.1 mg to about 2,500 mg of the inhibitor for a 70 kg patient per day, more commonly from about 2.5 mg to about 500 mg for a 70 kg patient per day.

Single or multiple administrations of the compositions can be carried out with dose levels and pattern being selected by the treating physician. In any event, the pharmaceutical formulations should provide a quantity of a RIOK3 inhibitor sufficient to effectively inhibit cellular signaling mediated by RIOK3 in the patient, either therapeutically or prophylatically.

V. Therapeutic Applications Using Nucleic Acids

A variety of conditions can be treated by therapeutic approaches that involve introducing a nucleic acid encoding a polypeptide inhibitor of RIOK3 signaling or small oligonucleotide sequence (such as antisense or miRNA) into a cell such that the coding sequence is transcribed and the polypeptide or oligonucleotide inhibitor is produced in the cell. For discussions on the application of gene therapy towards the treatment of genetic as well as acquired diseases, see, Miller *Nature* 357:455-460 (1992); and Mulligan *Science* 260:926-932 (1993).

A. Vectors for Gene Delivery

For delivery to a cell or organism, a polynucleotide encoding a polypeptide that inhibits RIOK3 signaling (such as a dominant negative mutant of RIOK3 or an inactivation RIOK3 antibody) or encoding an inhibitory oligonucleotide (such as antisense or miRNA) can be incorporated into a vector. Examples of vectors used for such purposes include expression plasmids capable of directing the expression of the nucleic acids in the target cell. In other instances, the vector is a viral vector system wherein the polynucleotide is incorporated into a viral genome that is capable of transfecting the target cell. In one embodiment, the encoding polynucleotide can be operably linked to expression and control sequences that can direct expression of the polypeptide or oligonucleotide in the desired target host cells. Thus, one can achieve expression of the polypeptide or oligonucleotide inhibitor under appropriate conditions in the target cell.

B. Gene Delivery Systems

Viral vector systems useful in the expression of a polypeptide or oligonucleotide inhibitor of RIOK3-mediate cellular signaling include, for example, naturally occurring or recombinant viral vector systems. Depending upon the particular application, suitable viral vectors include replication competent, replication deficient, and conditionally replicating viral vectors. For example, viral vectors can be derived from the genome of human or bovine adenoviruses, vaccinia virus, herpes virus, adeno-associated virus, minute virus of mice (MVM), HIV, sindbis virus, and retroviruses (including but not limited to Rous sarcoma virus and lentivirus), and MoMLV. Typically, the coding sequence of interest (e.g., one encoding for a polypeptide or oligonucleotide inhibitor of the present invention) are inserted into such vectors to allow packaging of the gene construct, typically with accompanying viral DNA, followed by infection of a sensitive host cell and expression of the coding sequence of interest.

As used herein, "gene delivery system" refers to any means for the delivery of a polynucleotide sequence of the invention to a target cell. In some embodiments of the invention, nucleic acids are conjugated to a cell receptor ligand for facilitated uptake (e.g., invagination of coated pits and internalization of the endosome) through an appropriate linking moiety, such as a DNA linking moiety (Wu et al., *J. Biol. Chem.* 263:14621-14624 (1988); WO 92/06180), or by ultrasound-microbubble delivery system (Lan H Y et al., *J. Am Soc. Nephrol.* 14:1535-1548). For example, nucleic acids can be linked through a polylysine moiety to asialo-oromucocid, which is a ligand for the asialoglycoprotein receptor of hepatocytes.

Similarly, viral envelopes used for packaging gene constructs that include the nucleic acids of the invention can be modified by the addition of receptor ligands or antibodies specific for a receptor to permit receptor-mediated endocytosis into specific cells (see, e.g., WO 93/20221, WO 93/14188, and WO 94/06923). In some embodiments of the invention, the DNA constructs of the invention are linked to viral proteins, such as adenovirus particles, to facilitate endocytosis (Curiel et al., *Proc. Natl. Acad. Sci.* U.S.A. 88:8850-8854 (1991)). In other embodiments, the inhibitors of the instant invention can include microtubule inhibitors (WO/9406922), synthetic peptides mimicking influenza virus hemagglutinin (Plank et al., *J. Biol. Chem.* 269:12918-12924 (1994)), and nuclear localization signals such as SV40 T antigen (WO93/19768).

Retroviral vectors may also be useful for introducing the coding sequence of a polypeptide or oligonucleotide inhibitor of the invention into target cells or organisms. Retroviral vectors are produced by genetically manipulating retroviruses. The viral genome of retroviruses is RNA. Upon infection, this genomic RNA is reverse transcribed into a DNA copy which is integrated into the chromosomal DNA of transduced cells with a high degree of stability and efficiency. The integrated DNA copy is referred to as a provirus and is inherited by daughter cells as is any other gene. The wild type retroviral genome and the proviral DNA have three genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site) (see, Mulligan, In: *Experimental Manipulation of Gene Expression*, Inouye (ed), 155-173 (1983); Mann et al., *Cell* 33:153-159 (1983); Cone and Mulligan, *Proceedings of the National Academy of Sciences*, U.S.A., 81:6349-6353 (1984)).

The design of retroviral vectors is well-known to those of ordinary skill in the art. In brief, if the sequences necessary for encapsidation (or packaging of retroviral RNA into infectious virions) are missing from the viral genome, the result is a cis acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including, e.g., European Patent Application EPA 0 178 220; U.S. Pat. No. 4,405,712; Gilboa *Biotechniques* 4:504-512 (1986); Mann et al., *Cell* 33:153-159 (1983); Cone and Mulligan *Proc. Natl. Acad. Sci.* USA 81:6349-6353 (1984); Eglitis et al. *Biotechniques* 6:608-614 (1988); Miller et al. *Biotechniques* 7:981-990 (1989); Miller (1992) supra; Mulligan (1993), supra; and WO 92/07943.

The retroviral vector particles are prepared by recombinantly inserting the desired nucleotide sequence into a retrovirus vector and packaging the vector with retroviral capsid proteins by use of a packaging cell line. The resultant retroviral vector particle is incapable of replication in the host cell but is capable of integrating into the host cell genome as a proviral sequence containing the desired nucleotide sequence. As a result, the patient is capable of producing, for example, a polypeptide or polynucleotide inhibitor of the invention and thus restore the target cells (e.g., erythroid cells) to a normal phenotype.

Packaging cell lines that are used to prepare the retroviral vector particles are typically recombinant mammalian tissue culture cell lines that produce the necessary viral structural proteins required for packaging, but which are incapable of producing infectious virions. The defective retroviral vectors that are used, on the other hand, lack these structural genes but encode the remaining proteins necessary for packaging. To prepare a packaging cell line, one can construct an infectious clone of a desired retrovirus in which the packaging site has been deleted. Cells comprising this construct will express all structural viral proteins, but the introduced DNA will be incapable of being packaged. Alternatively, packaging cell lines can be produced by transforming a cell line with one or more expression plasmids encoding the appropriate core and envelope proteins. In these cells, the gag, pol, and env genes can be derived from the same or different retroviruses.

A number of packaging cell lines suitable for the present invention are also available in the prior art. Examples of these cell lines include Crip, GPE86, PA317 and PG13 (see Miller et al., *J. Virol.* 65:2220-2224 (1991)). Examples of other packaging cell lines are described in Cone and Mulligan *Proceedings of the National Academy of Sciences*, USA, 81:6349-6353 (1984); Danos and Mulligan *Proceedings of the National Academy of Sciences*, USA, 85:6460-6464 (1988); Eglitis et al. (1988), supra; and Miller (1990), supra.

Packaging cell lines capable of producing retroviral vector particles with chimeric envelope proteins may be used. Alternatively, amphotropic or xenotropic envelope proteins, such as those produced by PA317 and GPX packaging cell lines may be used to package the retroviral vectors.

C. Pharmaceutical Formulations

When used for pharmaceutical purposes, the nucleic acid encoding a polypeptide or oligonucleotide RIOK3 inhibitor is generally formulated in a suitable buffer, which can be any pharmaceutically acceptable buffer, such as phosphate buffered saline or sodium phosphate/sodium sulfate, Tris buffer, glycine buffer, sterile water, and other buffers known to the ordinarily skilled artisan such as those described by Good et al. *Biochemistry* 5:467 (1966).

The compositions can additionally include a stabilizer, enhancer or other pharmaceutically acceptable carriers or vehicles. A pharmaceutically acceptable carrier can contain a physiologically acceptable compound that acts, for example, to stabilize the nucleic acids of the invention and any associated vector. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. Examples of carriers, stabilizers or adjuvants can be found in Remington's *Pharmaceutical Sciences*, Mack Publishing Company, Philadelphia, Pa., 17th ed. (1985).

D. Administration of Formulations

The formulations containing a polynucleotide sequence encoding a polypeptide or oligonucleotide inhibitor of RIOK3 can be delivered to target tissue or organ using any delivery method known to the ordinarily skilled artisan. In some embodiments of the invention, the encoding polynucleotide sequences are formulated for subcutaneous, intramuscular, intravenous, or intraperitoneal injection, or for oral ingestion or for topical application.

The formulations containing the nucleic acid of the invention are typically administered to a cell. The cell can be provided as part of a tissue, such as red blood cells as a part of the circulatory system, or as an isolated cell, such as in tissue culture. The cell can be provided in vivo, ex vivo, or in vitro.

The formulations can be introduced into the tissue of interest in vivo or ex vivo by a variety of methods. In some embodiments of the invention, the nucleic acids of the invention are introduced into cells by such methods as microinjection, calcium phosphate precipitation, liposome fusion, ultrasound, electroporation, or biolistics. In further embodiments, the nucleic acids are taken up directly by the tissue of interest, for example, when the targeted cells are the red blood cells intravenous injection is appropriate.

In some embodiments of the invention, the nucleic acids of the invention are administered ex vivo to cells or tissues explanted from a patient, then returned to the patient. Examples of ex vivo administration of therapeutic gene constructs include Nolta et al., *Proc Natl. Acad. Sci.* USA 93(6):2414-9 (1996); Koc et al., *Seminars in Oncology* 23(1):46-65 (1996); Raper et al., *Annals of Surgery* 223(2): 116-26 (1996); Dalesandro et al., *J. Thorac. Cardi. Surg.*, 11(2):416-22 (1996); and Makarov et al., *Proc. Natl. Acad. Sci.* USA 93(1):402-6 (1996).

Effective dosage of the formulations will vary depending on many different factors, including means of administration, target site, physiological state of the patient, and other medicines administered. Thus, treatment dosages will need to be titrated to optimize safety and efficacy. In determining the effective amount of the vector to be administered, the physician should evaluate the particular nucleic acid used, the disease state being diagnosed; the age, weight, and overall condition of the patient, circulating plasma levels, vector toxicities, progression of the disease, and the production of anti-vector antibodies. The size of the dose also will be determined by the existence, nature, and extent of any adverse side-effects that accompany the administration of a particular vector. To practice the present invention, doses of RIOK3 inhibitor such as midostaurin, axitinib, bosutinib, or ruxolitinib ranging from about 0.1 μg-100 mg per patient are typical. Doses generally range between about 0.01 and about 100 μg per kilogram of body weight, preferably between about 0.1 and about 50 μg/kg of body weight or about $10^8$-$10^{10}$ or $10^{12}$ particles per injection. In general, the dose equivalent of a naked nucleic acid from a vector is from about 1-100 μg for a typical 70 kg patient, and doses of vectors which include a retroviral particle are calculated to yield an equivalent amount of nucleic acid encoding a polypeptide or oligonucleotide that inhibits RIOK3-mediated signal transduction.

VI. Kits

The invention also provides kits for inhibiting RIOK3 signaling and therefore for treating beta-globinopathies according to the method of the present invention. The kits typically include a container that contains (1) a pharmaceutical composition having an effective amount of an inhibitor of RIOK3-mediated signaling (for instance, a dominant negative RIOK3 mutant, a polynucleotide sequence encoding the mutant polypeptide, a polynucleotide encoding an antisense or miRNA against RIOK3, an inactivating antibody of RIOK3, or a small molecule inhibitor of RIOK3 such as midostaurin, axitinib, bosutinib, or ruxolitinib) and (2) informational material containing instructions on how to dispense the pharmaceutical composition, including description of the type of patients who may be treated (e.g., human patients suffering from sickle cell disease or beta-thalassemia), the schedule (e.g., dose and frequency) and route of administration, and the like. In some cases, a second container is included in the kit to provide a second pharmaceutical composition comprising an effective amount of a second inhibitor of RIOK3.

EXAMPLES

The following examples are provided by way of illustration only and not by way of limitation. Those of skill in the art will readily recognize a variety of non-critical parameters that could be changed or modified to yield essentially similar results.

Example 1 Effects of RIOK3 Inhibition

Introduction

Increasing fetal hemoglobin expression above a certain threshold is potentially curative in beta-globinopathies. Previously, using conditional knockout mouse models and primary human hematopoietic stem cell (HSC) derived erythroid progenitor cells, the present inventors demonstrated that the potential transcription factor, C2H2 zinc finger protein POGZ is a negative regulator of mouse embryonic b-like globin and human fetal hemoglobin expression. Upon knockdown of POGZ in human erythroid progenitors, fetal hemoglobin expression is increased above 20% of total β-like globin, which is considered therapeutic. Additional repressors of fetal hemoglobin have been identified by others including BCL11A (Menzel S et al., *Nat Genet.* 2007, 39(10):1197-9) and LRF (Masuda T et al., *Science* 2016, 351(6270):285-9), and efforts at therapeutic targeting of these transcription factors have been vigorously pursued. However, transcription factors have been difficult to target for therapeutic purposes. Therefore, the inventors searched for a downstream target that would be easier to target with small molecular inhibitors. It was hypothesized that some of POGZ's downstream targets would lead to even greater fetal globin expression. Analysis of the potential downstream targets of POGZ by oligonucleotide arrays and RNA-sequencing identified Rio Kinase 3 (RIOK3) as significantly downregulated upon Pogz knockout in mice or POGZ knockdown in primary human erythroid progenitors. See FIG. 1.

Figure 2:
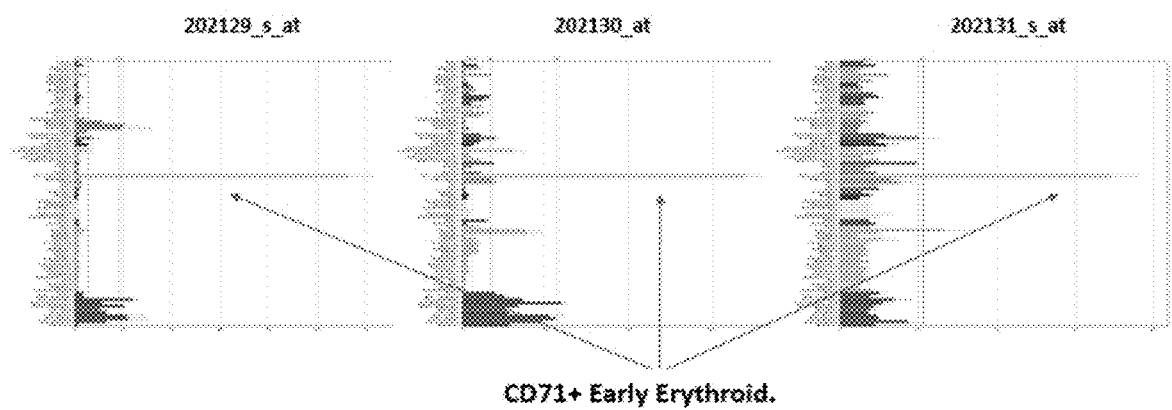
FIG. 2: RIOK3 is expressed in early adult erythroid cells according to the BioGPS database.
Figure 3:
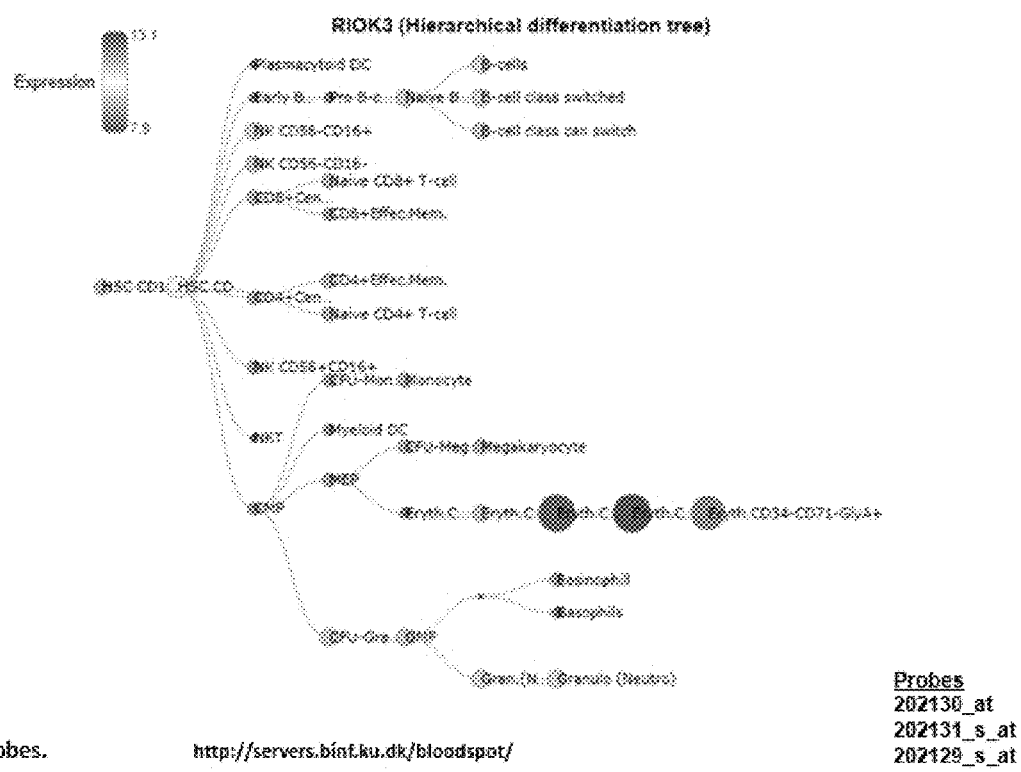
FIG. 3: RIOK3 expression is confined to developing erythroid cells in the Bloodspot database.

The expression pattern of RIOK3 in erythropoiesis according to the Bloodspot database (website: servers.binf ku.dk/bloodspot/) heightened interest in this target. According to the database, RIOK3 shows erythroid specific expression for 3 out of 4 probes but shows broader hematopoietic expression for one of the probes, suggesting erythroid specificity. See FIGS. 2 and 3.

Figure 4:
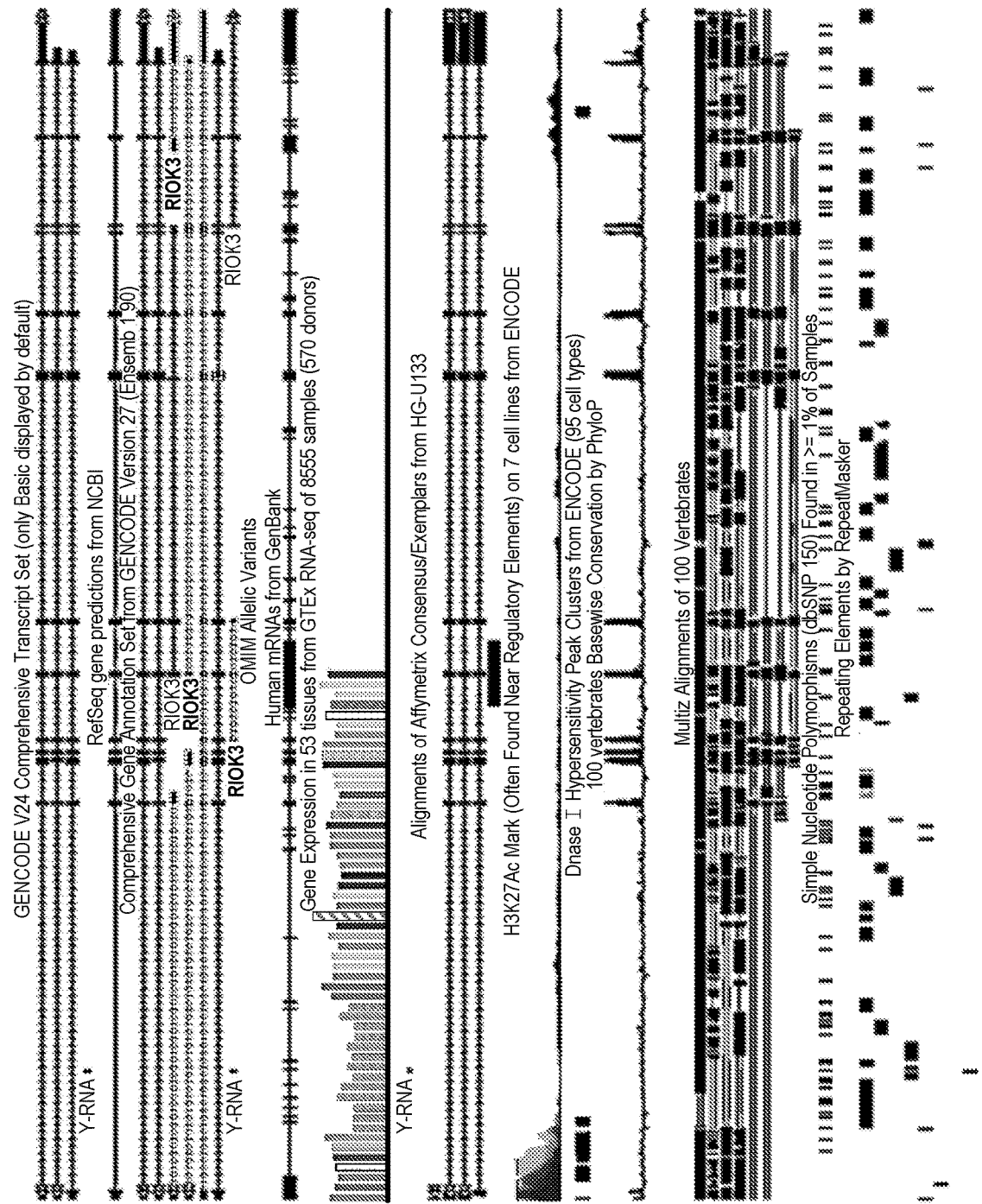
FIG. 4: RIOK3 is expected to have multiple transcription and translation variants.
Figure 5:
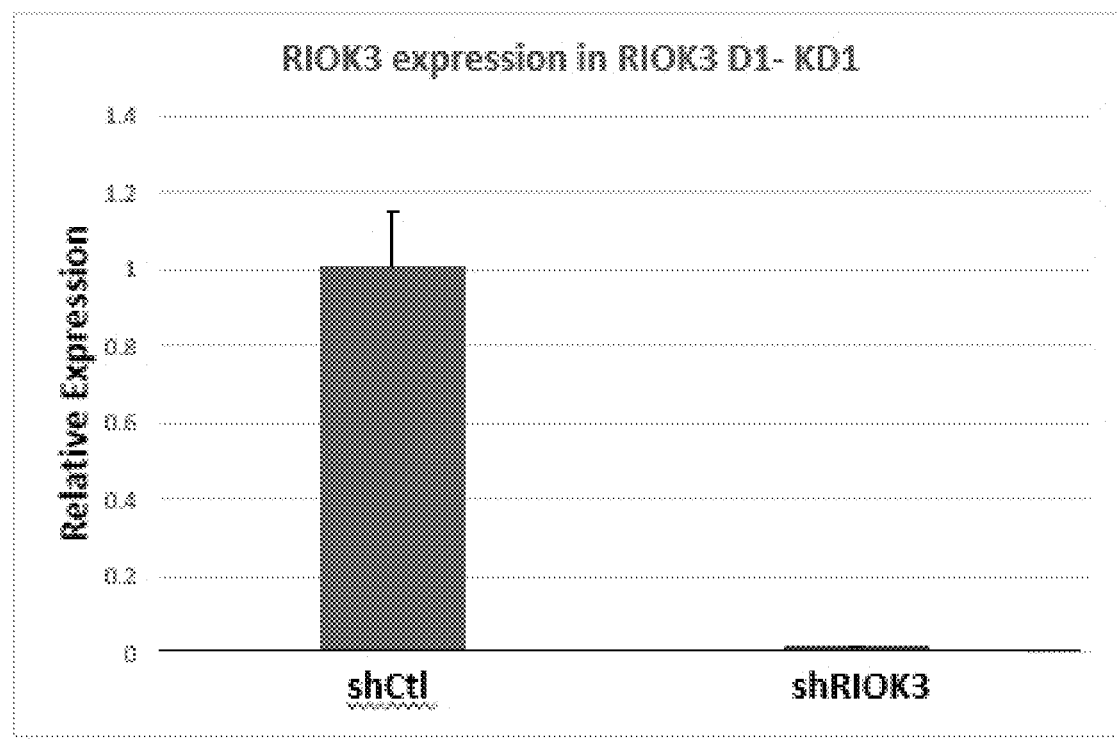
FIG. 5: Q-PCR shows decreased RIOK3 RNA expression on day 11 of culture (day 9) after shRNA knock down. CD34+ hematopoietic stem and progenitor cell derived erythroblasts were transduced on day 2 of culture with a control shRNA lentiviral vector (shCtl) or a RIOK3 specific lentiviral vector (shRIOK3) and RIOK3 expression analyzed on day 11 of culture.
Figure 6:
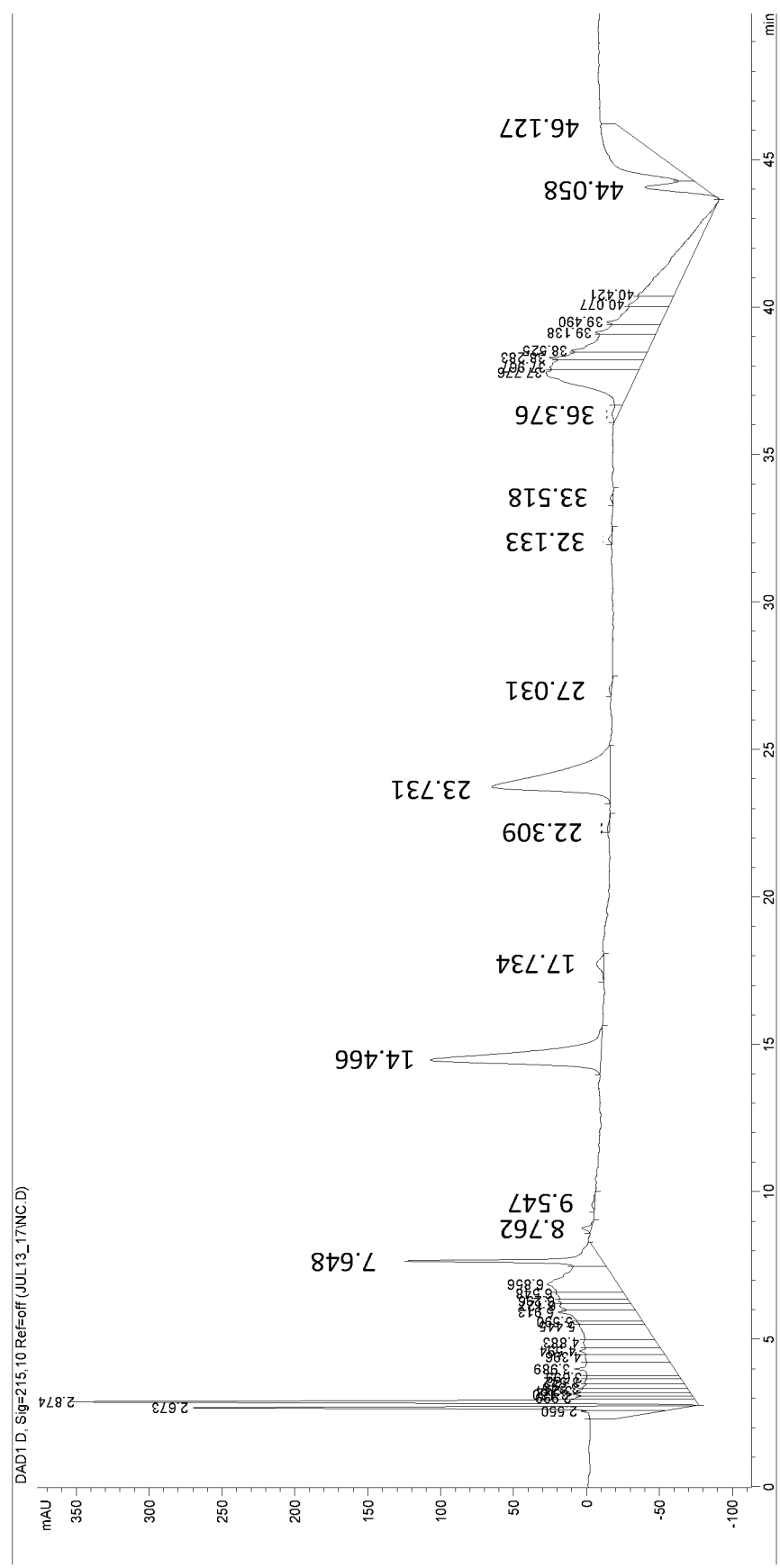
FIG. 6: RIOK3 knockdown results in marked upregulation of HbF expression. CD34+ hematopoietic stem and progenitor cell derived erythroblasts were transduced on day 2 of culture with a control shRNA lentiviral vector (shCtl; upper left panel) or a RIOK3 specific lentiviral vector (shRIOK3; upper right panel) and globin (HBB, HBA, HBE, HBG) levels analyzed on day 11 of culture by high performance liquid chromatography (HPLC) (bottom panel).
Figure 6:
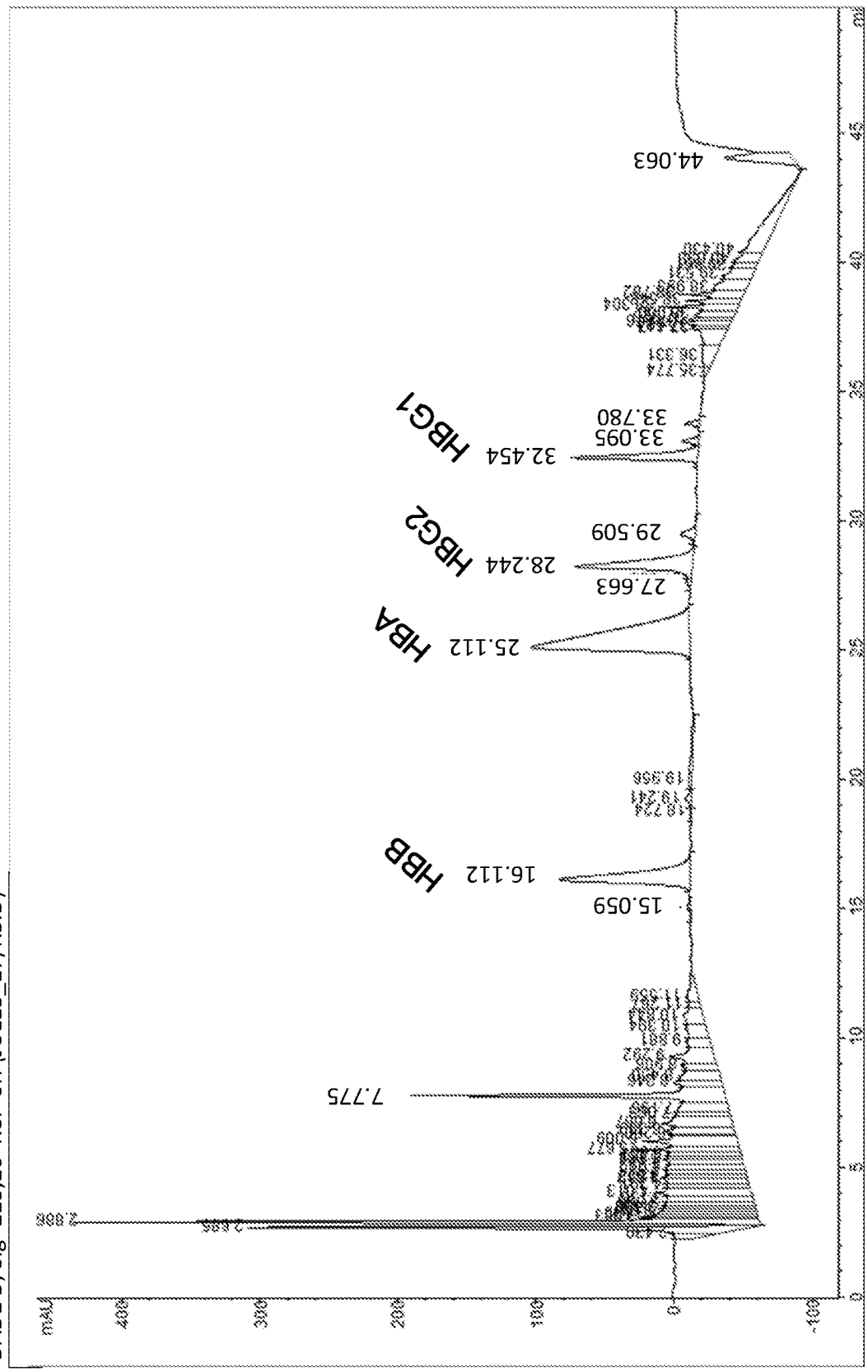
Figure 6:
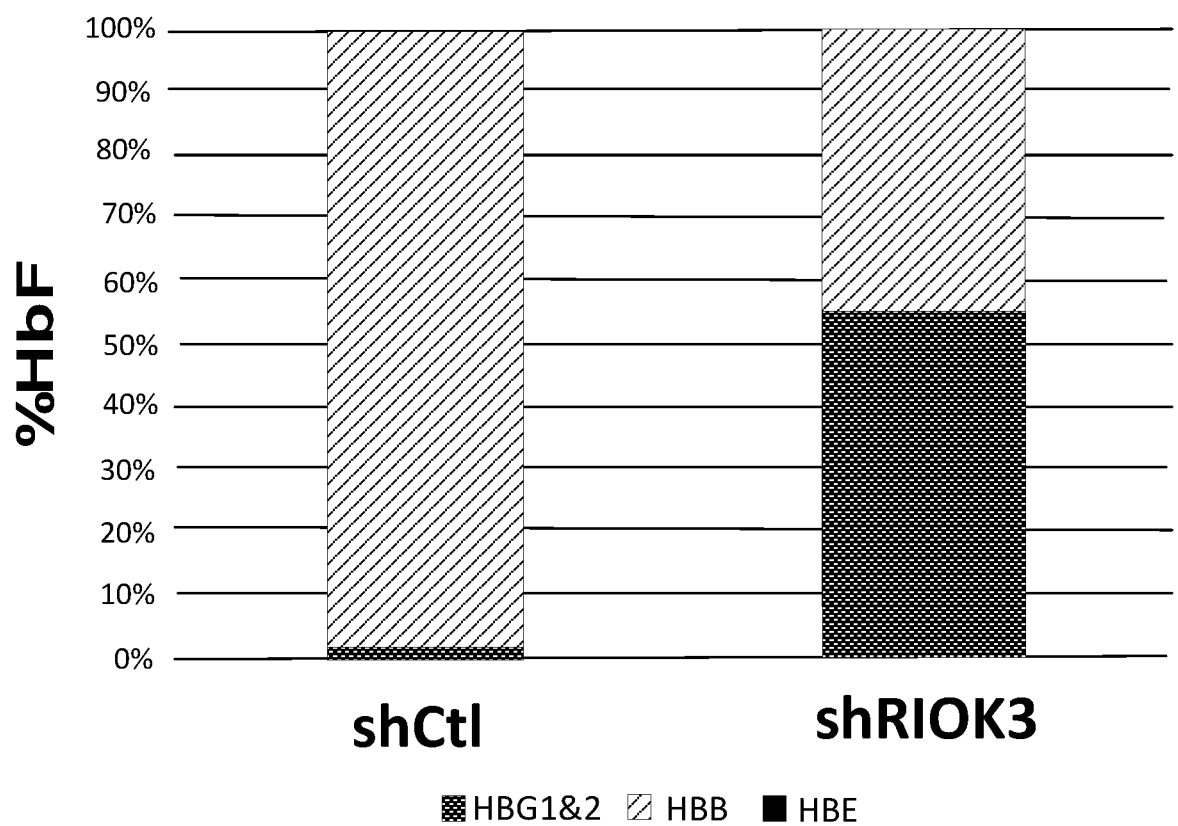
Figure 7:
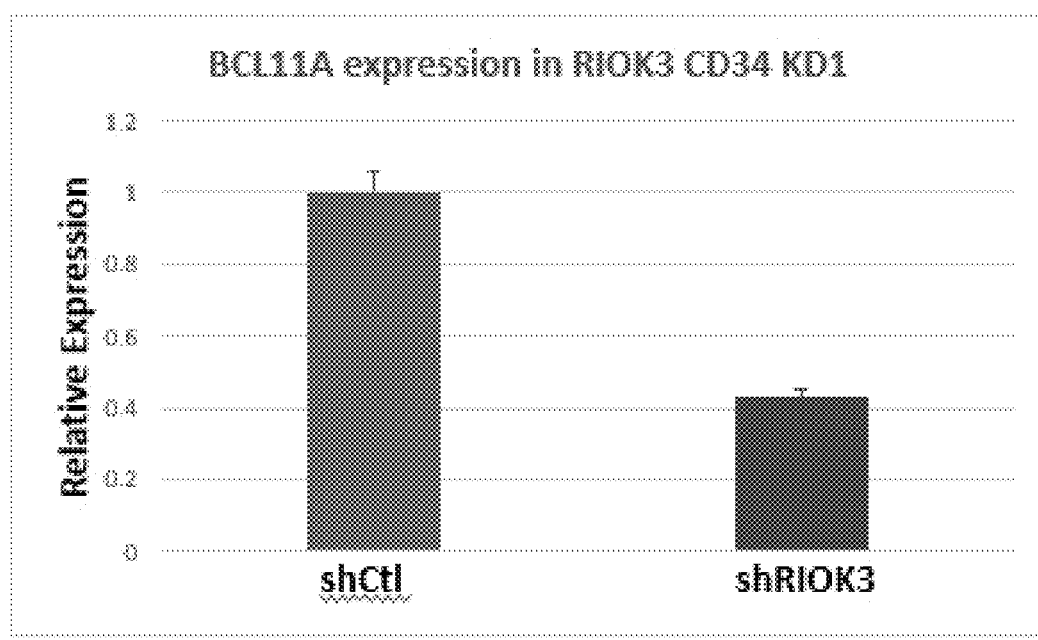
FIG. 7: RIOK3 knockdown results in significant downregulation of both BCL11A and LRF expression. CD34+ hematopoietic stem and progenitor cell derived erythroblasts were transduced on day 2 of culture with a control shRNA lentiviral vector (shCtl) or a RIOK3 specific lentiviral vector (shRIOK3) and BCL11A and LRF expression analyzed on day 11 of culture by Q-PCR.
Figure 7:
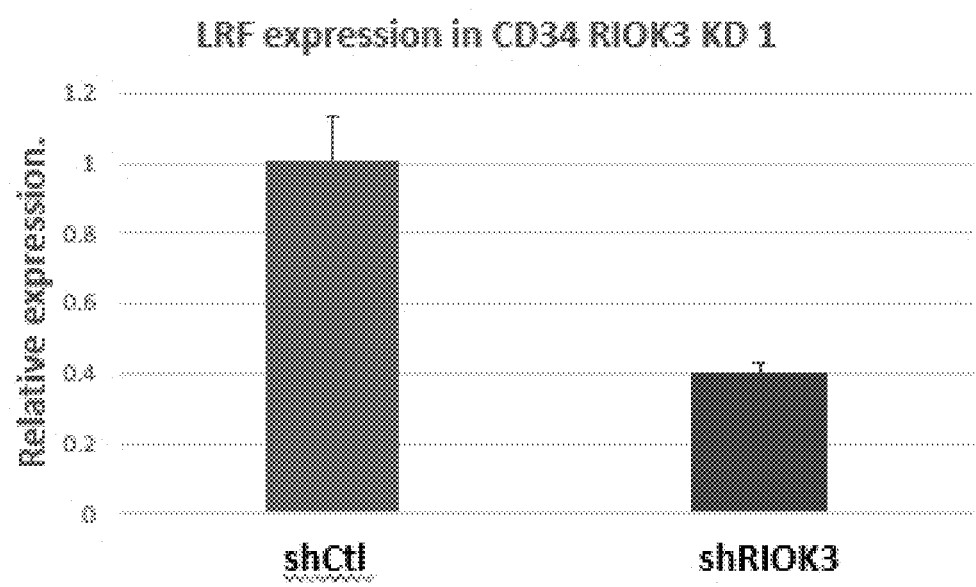
Figure 8:
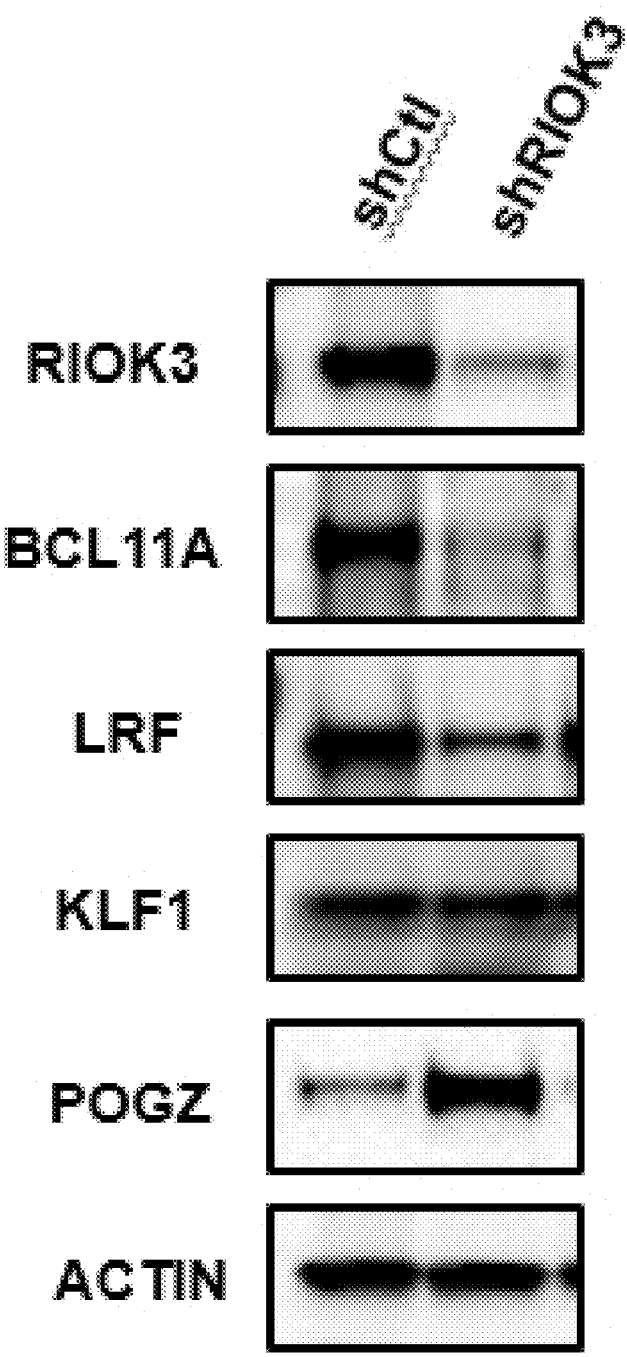
FIG. 8: Significant reduction in BCL11A and LRF protein levels upon RIOK3 knockdown in primary human erythroid progenitor cells. RIOK3 knockdown on day 6 of CD34+ cell culture, cells harvested on day 12. CD34+ hematopoietic stem and progenitor cell derived erythroblasts were transduced on day 2 of culture with a control shRNA lentiviral vector (shCtl) or a RIOK3 specific lentiviral vector (shRIOK3) and BCL11A and LRF protein levels analyzed on day 11 of culture by western blotting.
Figure 9:
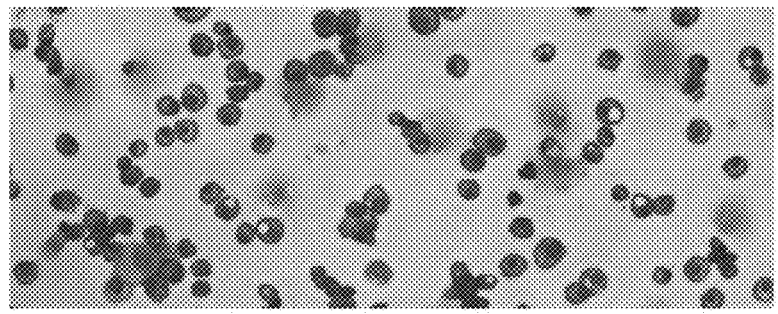
FIG. 9: Lentiviral mediated knockdown of RIOK3 in primary human CD34+ derived erythroid cells. Cytospin shows no morphicla differences on day 15 of culture. Cytospin shows no morphological differences on day 15 of culture between cells transduced with control shRNA (shCtl) vs cells transduced with RIOK3 specific shRNA (shRIOK3).
Figure 9:
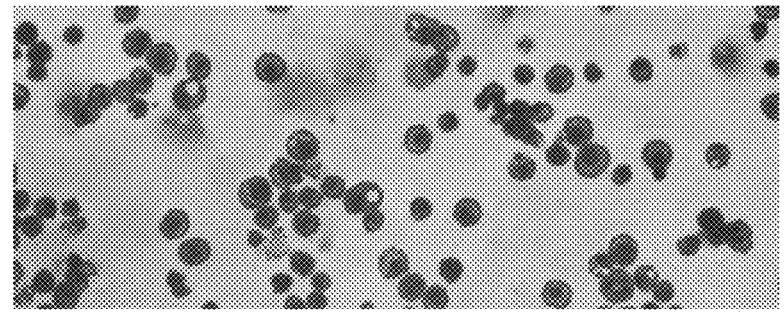

Genome browser Hg19 predicts 4 RIOK3 transcript variants and multiple RNA splice variants. Genome browser Hg38 predicts 3 RIOK3 transcript variants and also predicts multiple splice variants. See FIG. 4. Therefore, RIOK3 may have transcriptional or RNA splice variant specific expression in erythroid cells.

Very few publications reference RIOK3 and limited information is available on the function of RIOK3, but it has been implicated in innate immunity, cancer metastasis, and mouse erythroid cell enucleation (see selected publications in the reference list below). The preliminary data reported herein show that lentiviral mediated shRNA knockdown of RIOK3 in primary human erythroid progenitor cells increased fetal hemoglobin expression above 55% of total β-like globin expression, indicating its role as an important novel therapeutic target in beta-globinopathies.

The inventors then sought to determine if inhibition of the enzymatic activity of RIOK3 in erythroid cells is sufficient to increase fetal globin expression as knock out/knock down strategies involve highly technical, resource heavy interventions along with concerns regarding off target effects. Search for inhibitors of RIOK3 function revealed no commercially available inhibitors specifically targeting the enzyme. The present inventors thus analyzed the literature and pharmacological databases to determine if there were any leads on potential RIOK3 inhibitors. Based on Davis et al. 2011 publication (Comprehensive analysis of kinase inhibitor selectivity *Nat. Biotechnol.,* 29 (11): 1046-51) and (website: guidetopharmacology.org/GRAC/ObjectScreenDisplayForward?objectId=2188&familyId= 538&screenId=2), there are at least 16 inhibitors that show selectivity against RIOK3. Based on these data, 5 inhibitors were first chosen to be analyzed for their effects on RIOK3 function in primary human CD34 derived erythroid progenitor cells and whether they induced robust fetal hemoglobin expression. Some of the inhibitors chosen for the initial studies have already been FDA approved for treatment of other diseases, which should facilitate their use in treating beta-globinopathies once it is confirmed they are capable of inducing fetal hemoglobin expression above the therapeutic threshold. See FIG. 10.

Methods and Results

Quantitative PCR shows reduced RIOK3 RNA level after shRNA knockdown. CD34+ hematopoietic stem and progenitor cell derived erythroblasts were transduced on day 2 of culture with a control shRNA lentiviral vector (shCtl) or a RIOK3 specific lentiviral vector (shRIOK3) and RIOK3 expression analyzed on day 11 of culture by Q-PCR. The data shows that the RIOK3 shRNA efficiently targets and reduces RIOK3 RNA.

RIOK3 knockdown leads to upregulation of fetal beta-globin expression. CD34+ hematopoietic stem and progenitor cell derived erythroblasts were transduced on day 2 of culture with a control shRNA lentiviral vector (shCtl) or a RIOK3 specific lentiviral vector (shRIOK3) and globin (HBB, HBA, HBE, HBG) levels analyzed on day 11 of culture by high performance liquid chromatography (HPLC). % HbF was calculated by dividing HBG1+HBG2 values with total β-globin (HBB+HBE+HBG1+HBG2) values. The data shows that upon RIOK3 knockdown the levels of fetal β-globins HBG1 and HBG2 are robustly increased compared to control.

RIOK3 knockdown leads to downregulation of BCL11A and LRF expression. CD34+ hematopoietic stem and progenitor cell derived erythroblasts were transduced on day 2 of culture with a control shRNA lentiviral vector (shCtl) or a RIOK3 specific lentiviral vector (shRIOK3) and BCL11A and LRF expression analyzed on day 11 of culture by Q-PCR. The data shows that upon RIOK3 knockdown the fetal hemoglobin repressors BCL11A and LRF are significantly downregulated at the transcriptional level.

RIOK3 knockdown leads to downregulation of BCL11A and LRF protein expression in erythroid progenitor cells. CD34+ hematopoietic stem and progenitor cell derived erythroblasts were transduced on day 2 of culture with a control shRNA lentiviral vector (shCtl) or a RIOK3 specific lentiviral vector (shRIOK3) and BCL11A and LRF protein levels analyzed on day 11 of culture by western blotting. The data shows that BCL11A and LRF protein levels are significantly reduced upon RIOK3 knockdown compared to control.

RIOK3 knockdown in primary CD34+ derived erythroid cells. Cytospin shows no morphological differences on day 15 of culture between cells transduced with control shRNA vs cells transduced with RIOK3 specific shRNA. CD34+ hematopoietic stem and progenitor cell derived erythroblasts were transduced on day 2 of culture with a control shRNA lentiviral vector (shCtl) or a RIOK3 specific lentiviral vector (shRIOK3) and spun on glass slides and stained with the HEMA 3 manual staining system.

Discussions

Further efforts will be devoted to produce RIOK3 specific inhibitors and analyze the effect of RIOK3 enzyme activity inhibition on erythroid cell growth, differentiation, enucleation, and fetal hemoglobin expression. Further, inhibition of RIOK3 will be studied through gene transfer, gene edition, or through an orally bioavailable kinase inhibitor with aim to result in high levels of fetal hemoglobin sufficient to correct the beta-globinopathies. More specific goals include: (1) developing shRNA targeting RIOK3 gene therapy strategies to increase fetal hemoglobin using erythroid specific lentiviral vectors among human CD34+ cells; (2) developing gene editing strategies for disruption of RIOK3 gene using CRISPR/Cas9 or other endonucleases among human CD34+ cells; and (3) developing RIOK3-specific kinase inhibitors through existing databases and collaborators as a potential orally bioavailable treatment.

Example 2: Primate Study

Midostaurin (RYDAPT®) is tested in a non-human primate study. Animals are dosed daily with the oral formulation and monitored for effects on hbg expression. Specifically, the 1-2 mL contents of a 25 mg Midostaurin (RYDAPT®) capsule (also containing macrogolglycerol hydroxystearate, gelatin, macrogol, glycerol, ethanol anhydrous, maize oil mono-di-triglycerides, titanium dioxide (E171), all-rac-alpha-tocopherol, iron oxide yellow (E172), iron oxide red (E172), carmine (E120), hypromellose, propylene glycol, and purified water) are mixed into a vehicle of crushed monkey crunch and fruit additives, and it is given orally to the animals as a treat twice a day for a period of two months. Following NHLBI ACUC (Animal Care and User Committee) approved protocol H-0330, treatment is given to four specific pathogen free (SPF) rhesus macaques (identification codes ZL37, RC808, ZJ34, and RQ4753). Three other SPF rhesus macaques (identification codes RQ6595, RA0462, and 1104220) serve as controls, receiving vehicle alone. Once weekly, after the morning dose is given, a complete blood count, serum biochemistry, and a 5 mL Acid Citrate Dextrose (ACD) blood sample are taken. All four monkeys receiving treatment are compliant throughout the two-month period.

An erythroid specific RIOK3 CrispR cas9 lentivirus as well as a mouse-specific RIOK3 shRNA lentivirus have been designed and built for further testing in animals.

All patents, patent applications, and other publications, including GenBank Accession Numbers or similar sequence identification numbers, cited in this application are incorporated by reference in the entirety of their contents for all purposes.

REFERENCES

1. Weinberg F, Reischmann N, Fauth L, Taromi S, Mastroianni J, Köhler M, Halbach S, Becker A C, Deng N, Schmitz T, Uhl F M, Herbener N, Riedel B, Beier F, Swarbrick A, Lassmann S, Dengjel J, Zeiser R, Brummer T. The Atypical Kinase RIOK1 Promotes Tumor Growth and Invasive Behavior. EBioMedicine. 2017 June; 20:79-97. doi: 10.1016/j.ebiom.2017.04.015. Epub 2017 Apr. 12. PubMed PMID: 28499923; PubMed Central PMCID: PMC5478185.
2. Maasalu K, Laius O, Zhytnik L, Kõks S, Prans E, Reimann E, Märtson A. Featured Article: Transcriptional landscape analysis identifies differently expressed genes involved in follicle-stimulating hormone induced postmenopausal osteoporosis. Exp Biol Med (Maywood). 2017 January; 242(2):203-213. doi: 10.1177/1535370216679899. Epub 2016 Nov. 20. PubMed PMID: 27856519; PubMed Central PMCID: PMC5167124.
3. Oshiumi H, Kouwaki T, Seya T. Accessory Factors of Cytoplasmic Viral RNA Sensors Required for Antiviral Innate Immune Response. Front Immunol. 2016 May 25; 7:200. doi: 10.3389/fimmu.2016.00200. eCollection 2016. Review. PubMed PMID: 27252702; PubMed Central PMCID: PMC4879126.
4. Takashima K, Oshiumi H, Seya T. RIOK3 keeps MDA5 inactive. Oncotarget. 2015 Oct. 13; 6(31):30423-4. doi: 10.18632/oncotarget.5265. PubMed PMID: 26415216; PubMed Central PMCID: PMC4741529.
5. Haring R, Schurmann C, Homuth G, Steil L, Völker U, Völzke H, Keevil B G, Nauck M, Wallaschofski H. Associations between Serum Sex Hormone Concentrations and Whole Blood Gene Expression Profiles in the General Population. PLoS One. 2015 May 22; 10(5):e0127466. doi: 10.1371/journal.pone.0127466. eCollection 2015. PubMed PMID: 26001193; PubMed Central PMCID: PMC4441431.
6. Takashima K, Oshiumi H, Takaki H, Matsumoto M, Seya T. RIOK3-mediated phosphorylation of MIDA5 interferes with its assembly and attenuates the innate immune response. Cell Rep. 2015 Apr. 14; 11(2):192-200. PubMed PMID: 25865883.
7. Singleton D C, Rouhi P, Zois C E, Haider S, Li J L, Kessler B M, Cao Y, Harris A L. Hypoxic regulation of RIOK3 is a major mechanism for cancer cell invasion and metastasis. Oncogene. 2015 Sep. 3; 34(36):4713-22. doi: 10.1038/onc.2014.396. Epub 2014 Dec. 8. PubMed PMID: 25486436; PubMed Central PMCID: PMC4430306.
8. Feng J, De Jesus P D, Su V, Han S, Gong D, Wu N C, Tian Y, Li X, Wu T T, Chanda S K, Sun R. RIOK3 is an adaptor protein required for IRF3-mediated antiviral type I interferon production. J Virol. 2014 July; 88(14):7987-97. doi: 10.1128/JVI.00643-14. Epub 2014 May 7. PubMed PMID: 24807708; PubMed Central PMCID: PMC4097797.
9. Tariki M, Wieczorek S A, Schneider P, Banfer S, Veitinger S, Jacob R, Fendrich V, Lauth M. RIO kinase 3 acts as a SUFU-dependent positive regulator of Hedgehog signaling. Cell Signal. 2013 December; 25(12):2668-75. doi: 10.1016/j.cellsig.2013.08.037. Epub 2013 Sep. 7. PubMed PMID: 24018050.
10. Baumas K, Soudet J, Caizergues-Ferrer M, Faubladier M, Henry Y, Mougin A. Human RioK3 is a novel component of cytoplasmic pre-40S pre-ribosomal particles. RNA Biol.

11. Zhang L, Flygare J, Wong P, Lim B, Lodish H F. miR-191 regulates mouse erythroblast enucleation by down-regulating Riok3 and Mxi1. Genes Dev. 2011 Jan. 15; 25(2):119-24. doi: 10.1101/gad.1998711. Epub 2010 Dec. 31. PubMed PMID: 21196494; PubMed Central PMCID: PMC3022257.

12. Kalinina T, Güngör C, Thieltges S, Möller-Krull M, Penas E M, Wicklein D, Streichert T, Schumacher U, Kalinin V, Simon R, Otto B, Dierlamm J, Schwarzenbach H, Effenberger K E, Bockhorn M, Izbicki J R, Yekebas E F. Establishment and characterization of a new human pancreatic adenocarcinoma cell line with high metastatic potential to the lung. BMC Cancer. 2010 Jun. 16; 10:295. doi: 10.1186/1471-2407-10-295. PubMed PMID: 20553613; PubMed Central PMCID: PMC2927995.

13. Mishra D K, Chen Z, Wu Y, Sarkissyan M, Koeffler H P, Vadgama J V. Global methylation pattern of genes in androgen-sensitive and androgen-independent prostate cancer cells. Mol Cancer Ther. 2010 January; 9(1):33-45. doi: 10.1158/1535-7163.MCT-09-0486. Epub 2010 Jan. 6. PubMed PMID: 20053773; PubMed Central PMCID: PMC2806502.

14. Shan J, Wang P, Zhou J, Wu D, Shi H, Huo K. RIOK3 interacts with caspase-10 and negatively regulates the NF-kappaB signaling pathway. Mol Cell Biochem. 2009 December; 332(1-2):113-20. doi: 10.1007/s11010-009-0180-8. Epub 2009 Jun. 26. PubMed PMID: 19557502.

15. Kimmelman A C, Hezel A F, Aguirre A J, Zheng H, Paik J H, Ying H, Chu G C, Zhang J X, Sahin E, Yeo G, Ponugoti A, Nabioullin R, Deroo S, Yang S, Wang X, McGrath J P, Protopopova M, Ivanova E, Zhang J, Feng B, Tsao M S, Redston M, Protopopov A, Xiao Y, Futreal P A, Hahn W C, Klimstra D S, Chin L, DePinho R A. Genomic alterations link Rho family of GTPases to the highly invasive phenotype of pancreas cancer. Proc Natl Acad Sci USA. 2008 Dec. 9; 105(49):19372-7. doi: 10.1073/pnas.0809966105. Epub 2008 Dec. 2. PubMed PMID: 19050074; PubMed Central PMCID: PMC2614768.

SEQUENCE LISTING

SEQ ID NO: 1 Homo sapiens RIO kinase 3 (RIOK3),
transcript variant 1, mRNA NCBI Reference
Sequence: NM_003631.4
GenBank Graphics
>NM_003831.4:220-1779 Homo sapiens RIO kinase 3
(RIOK3), transcript variant 1, mRNA
ATGGATCTGGTAGGAGTGGCATCGCCTGAGCCCGGGACGGCAGCGGCCTG
GGGACCCAGCAAGTGTCCATGGGCTATTCCTCAAAATACAATATCTTGTT
CTTTGGCTGATGTAATGAGTGAACAGCTGGCCAAAGAATTGCAGTTAGAA
GAAGAAGCTGCCGTTTTTCCTGAAGTTGCTGTTGCTGAAGGACCATTTAT
TACTGGAGAAAACATTGATACTTCCAGTGACCTTATGCTGGCTCAGATGC
TACAGATGGAATATGACAGAGAATATGATGCACAGCTTAGGCGTGAAGAA
AAAAAATTCAATGGAGATAGCAAAGTTTCCATTTCCTTTGAAAATTATCG
AAAAGTGCATCCTTATGAAGACAGCGATAGCTCTGAAGATGAGGTTGACT
GGCAGGATACTCGTGATGATCCCTACAGACCAGCAAAACCGGTTCCCACT
CCTAAAAAGGGCTTTATTGGAAAAGGAAAAGATATCACCACCAAACATGA
TGAAGTAGTATGTGGGAGAAAGAACACAGCAGAAGAATGGAAAATTTGCAC
CTGAGTTTCAGGTAGGAGATGGAATTGGAATGGATTTAAAACTATCAAAC
CATGTTTTCAATGCTTTAAAACAACATGCCTACTCAGAAGAACGTCGAAG
TGCCCGCCTACATGAGAAAAGGAGCATTCTACAGCAGAAAAGCAGTTG
ATCCTAAGACACGTTTACTTATGTATAAAATGGTCAACTCTGGAATGTTG
GAGACAATCACTGGCTGTATTAGTACAGGAAAGGAGTCTGTTGTCTTTCA
TGCATATGGAGGGAGCATGGAGGATGAAAAGGAAGATAGTAAAGTTATAC
CTACAGAATGTGCCATCAAGGTATTTAAAACAACCCTTAATGAATTTAAG
AATCGTGACAAATATATTAAAGATGATTTCAGGTTTAAAGATCGCTTCAG
TAAACTAAATCCACGTAAGATCATCCGCATGTGGGCAGAAAAAGAAATGC
ACAATCTCGCAAGAATGCAGAGAGCTGGAATTCCTTGTCCAACAGTTGTA
CTACTGAAGAAACACATTTTAGTTATGTCTTTTATTGGCCATGATCAAGT
TCCAGCCCCTAAATTAAAAGAAGTAAAGCTCAATAGTGAAGAAATGAAAG
AAGCCTACTATCAAACTCTTCATTTGATGCGGCAGTTATATCATGAATGT
ACGCTTGTCCATGCTGACCTCAGTGAGTATAACATGCTGTGGCATGCTGG
AAAGGTCTGGTTGATCGATGTCAGTCAGTCAGTAGAACCTACCCACCCTC
ACGGCCTGGAGTTCTTGTTCCGGGACTGCAGGAATGTCTCGCAGTTTTTC
CAGAAAGGAGGAGTCAAGGAAGCCCTTAGTGAACGAGAACTCTTCAATGC
TGTTTCAGGCTTAAACATCACAGCAGATAATGAAGCTGATTTTTTAGCTG
AGATAGAAGCTTTGGAGAAAATGAATGAAGATCACGTTCAGAAGAATGGA
AGGAAAGCTGCTTCATTTTTGAAAGATGATGGAGACCCACCACTACTATA
TGATGAATAG SEQ ID NO: 2
Amino acid sequence of Homo sapiens RIO kinase 3
(RIOK3), mRNA. (from RefSeq NM_003831)
Gencode Transcript: ENST00000339486.7
Gencode Gene: ENSG00000101782.14
>uc002kui.5 (RIOK3) length = 519
MDLVGVASPEPGTAAAWGPSKCPWAIPQNTISCSLADVMSEQLAKELQLE
EEAAVFPEVAVAEGPFITGENIDISSDLMLAQMLQMEYDREYDAQLRREE
KKENGDSKVSISFENYRKVHPYEDSDSSEDEVDWQDTRDDPYRPAKPVPI
PKKGFIGKGKDITTKHDEVVCGRKNTARMENFAPEFQVGDGIGMDLKLSN
HVFNALKQHAYSEERRSARLHEKKEHSTAEKAVDPKTRLLMYKMVNSGML
ETITGCISIGKESVVEHAYGGSMEDEKEDSKVIPTECAIKVEKTILNEFK
NRDKYIKDDFRFKDRFSKLNPRKIIRMWAEKEMHNLARMQRAGIPCPTVV
LLKKHILVMSFIGHDQVPAPKLKEVKLNSEEMKEAYYQTLHLMRQLYHEC
TLVHADLSEYNMLWHAGKVWLIDVSQSVEPTHPHGLEFLFRDCRNVSQFF
QKGGVKEALSERELFNAVSGLNITADNEADFLAEIEALEKMNEDHVQKNG
RKAASFLKDDGDPPLLYDE SEQ ID NO: 3
Amino acid sequence of Homo sapiens RIO kinase 3
(RIOK3), mRNA. (from RefSeq NM_003831)
Gencode Transcript: ENST00000581585.5
Gencode Gene: ENSG00000101782.14
>uc010xas.3 (RIOK3) length = 503
MDLVGVASPEPGTAAAWGPSKCPWAIPQNTISCSLADVMSEQLAKELQLE
EEAAVFPEVADLMLAQMLQMEYDREYDAQLRREEKKENGDSKVSISFENY
RKVHPYEDSDSSEDEVDWQDTRDDPYRPAKPVPIPKKGFIGKGKDITTKH
DEVVCGRKNTARMENFAPEFQVGDGIGMDLKLSNHVFNALKQHAYSEERR
SARLHEKKEHSTAEKAVDPKTRLLMYKMVNSGMLETITGCISIGKESVVF
HAYGGSMEDEKEDSKVIPTECAIKVFKITLNEFKNRDKYIKDDFRFKDRF
SKLNPRKIIRMWAEKEMHNLARMQRAGIPCPTVVLLKKHILVMSFIGHDQ
VPAPKLKEVKLNSEEMKEAYYQTLHLMRQLYHECTLVHADLSEYNMLWHA
GKVWLIDVSQSVEPTHPHGLEFLFRDCRNVSQFFQKGGVKEALSERELFN
AVSGLNITADNEADFLAEIEALEKMNEDHVQKNGRKAASFLKDDGDPPLL
YDE SEQ ID NO: 4
Amino acid sequence of Homo sapiens RIO kinase 3
(RIOK3), mRNA. (from RefSeq NM_003831)
Gencode Transcript: ENST00000577501.5
Gencode Gene: ENSG00000101782.14
>uc010dls.4 (RIOK3) length = 516
MDLVGVASPEPGTAAAWGPSKCPWAIPQNTISCSLADVMSEQLAKELQLE
EEAAVFPEVAVAEGPFITGENIDISSDLMLAQMLQMEYDREYDAQLRREE
KKENGDSKVSISFENYRKVHPYEDSDSSEDEVDWQDTRDDPYRPAKPVPI
PKKGFIGKGKDITTKHDEVVCGRKNTARMENFAPEFQVGDGIGMDLKLSN
HVFNALKQHAYSEERRSARLHEKKEHSTAEKAVDPKTRLLMYKMVNSGML
ETITGCISIGKESVVEHAYGGSMEDEKEDSKVIPTECAIKVEKTILNEFK
NRDKYIKDDFRFKDRFSKLNPRKIIRMTNAEKEMHNLARMQRAGIPCPTV
VLLKKHILVMSFIGHDQVPAPKLKEVKLNSEEMKEAYYQTLHLMRQLYHE
CTLVHADLSEYNMLYNHAGKVTNLIDVSQSVEPTHPHGLEFLFRDCRNVS
QKGGVKEALSERELFNAVSGLNITADNEADFLAEIEALEKMNEDHVQKNG
RKAASFLKDDGDPPLLYDE

What is claimed is:

1. A method for promoting gamma-globin synthesis in an erythroid cell of a patient that has been diagnosed with a beta-globinopathy, the method comprising contacting the cell with an effective amount of an inhibitor of RIOK3, wherein the inhibitor of RIOK3 is Midostaurin.

2. The method of claim 1, wherein the cell is within the body of a human patient.

3. The method of claim 2, comprising administering the effective amount of the inhibitor of RIOK3 to the patient.

4. The method of claim 3, wherein the inhibitor of RIOK3 is administered by subcutaneous, intramuscular, intravenous, intraperitoneal, or oral administration.

5. The method of claim 3, wherein the inhibitor of RIOK3 is administered in the form of a solution, a powder, a paste, a tablet, or a capsule.

6. The method of claim 1, wherein the beta-globinopathy is selected from the group consisting of sickle cell disease and beta-thalassemia.

7. A method for treating a beta-globinopathy in a subject in need thereof, the method comprising administering to the subject a therapeutically-effective amount of an inhibitor of RIOK3, wherein the inhibitor of RIOK3 is Midostaurin.

8. The method of claim 7, wherein the subject is a human.

9. The method of claim 7, wherein the patient has been diagnosed with a beta-globinopathy selected from the group consisting of sickle cell disease and beta-thalassemia.

10. The method of claim 7, wherein the inhibitor of RIOK3 is comprised in a composition.

11. The method of claim 7, wherein the inhibitor of RIOK3 is administered by subcutaneous, intramuscular, intravenous, intraperitoneal, or oral administration.

12. The method of claim 7, wherein the inhibitor of RIOK3 is administered in the form of a solution, a powder, a paste, a tablet, or a capsule.

* * * * *